US008805525B2

(12) United States Patent
Gerber et al.

(10) Patent No.: US 8,805,525 B2
(45) Date of Patent: Aug. 12, 2014

(54) THERAPY PROGRAM MODIFICATION BASED ON AN ENERGY THRESHOLD

(71) Applicant: Medtronic, Inc., Minneapolis, MN (US)

(72) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/042,108

(22) Filed: Sep. 30, 2013

(65) Prior Publication Data

US 2014/0031900 A1 Jan. 30, 2014

Related U.S. Application Data

(63) Continuation of application No. 12/989,726, filed as application No. PCT/US2009/031967 on Jan. 26, 2009, now Pat. No. 8,548,596.

(60) Provisional application No. 61/048,774, filed on Apr. 29, 2008.

(51) Int. Cl.
*A61N 1/00* (2006.01)
(52) U.S. Cl.
USPC .................................. 607/59; 607/46; 607/60
(58) Field of Classification Search
USPC ................................................ 607/46, 59–60
See application file for complete search history.

(56) References Cited

U.S. PATENT DOCUMENTS

| 5,501,703 | A | 3/1996 | Holsheimer et al. |
| 5,643,330 | A | 7/1997 | Holsheimer et al. |
| 5,713,922 | A | 2/1998 | King |
| 5,800,465 | A | 9/1998 | Thompson et al. |
| 5,925,070 | A | 7/1999 | King et al. |
| 6,083,252 | A | 7/2000 | King et al. |
| 6,895,280 | B2 | 5/2005 | Meadows et al. |
| 6,988,006 | B2 | 1/2006 | King et al. |
| 8,548,596 | B2 | 10/2013 | Gerber et al. |
| 2003/0018370 | A1 | 1/2003 | King et al. |
| 2003/0120323 | A1 | 6/2003 | Meadows et al. |
| 2006/0017749 | A1 | 1/2006 | McIntyre et al. |
| 2006/0149337 | A1 | 7/2006 | John |
| 2006/0259097 | A1 | 11/2006 | Hickman et al. |
| 2011/0040352 | A1 | 2/2011 | Gerber et al. |

OTHER PUBLICATIONS

International Search Report and Written Opinion for counterpart international application No. PCT/US2009/031967, dated Aug. 5, 2009, 12 pages.
International Preliminary Report on Patentability for counterpart international application No. PCT/US2009/031967, dated Nov. 11, 2010, 7 pages.
Prosecution History from U.S. Appl. No. 12/989,726, dated Sep. 21, 2012 through May 30, 2013, 40 pages.

*Primary Examiner* — Nicole F Lavert
(74) *Attorney, Agent, or Firm* — Shumaker & Sieffert, P.A.

(57) ABSTRACT

A therapy program is modified to decompose an electrical stimulation signal defined by the therapy program into a plurality of subsignals based on a comparison between an energy associated with the stimulation signal and a threshold value. An electrical stimulation signal defined by a therapy program may be decomposed into a plurality of subsignals when an electrical stimulation energy of the stimulation signal exceeds the maximum energy output of the medical device or of a channel of the medical device. The energy associated with each one of the subsignals may be less than the energy threshold value of the medical device.

20 Claims, 16 Drawing Sheets

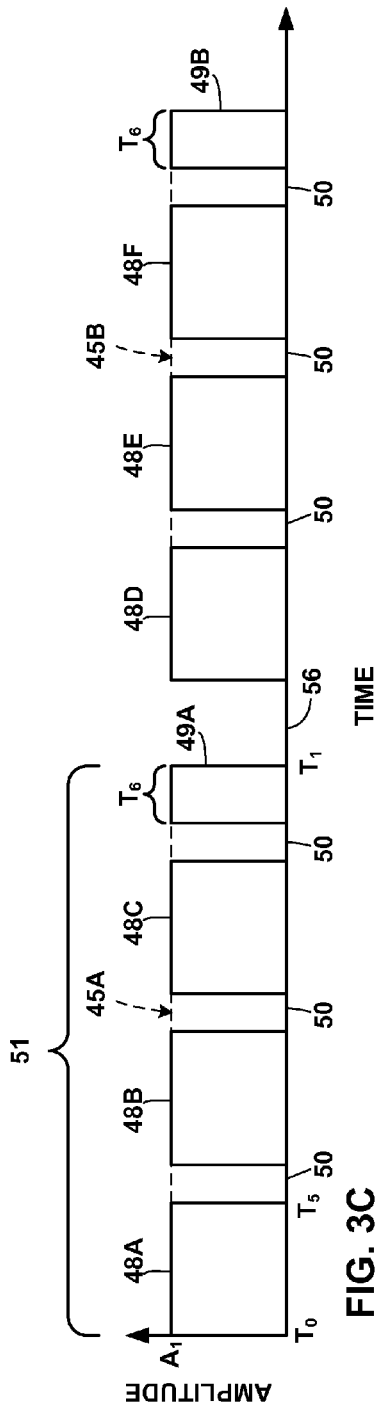
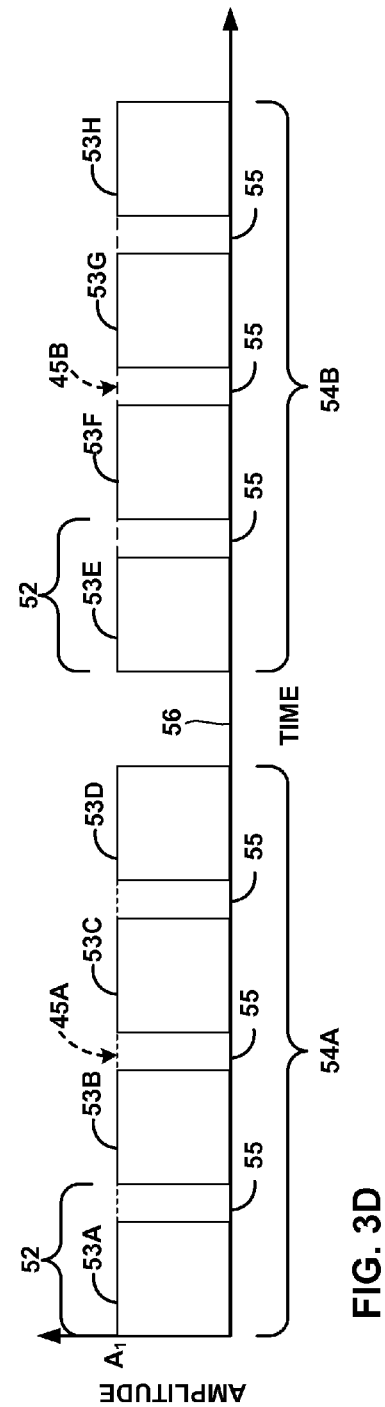
FIG. 3C
FIG. 3D

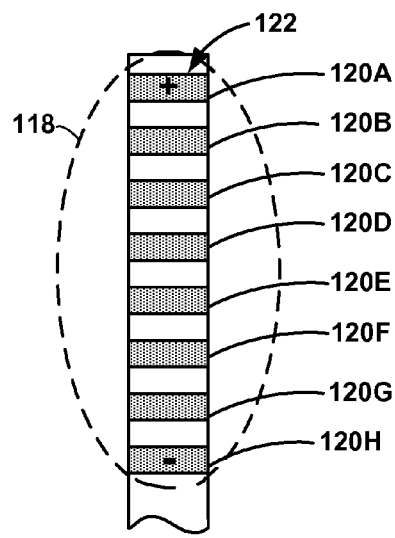
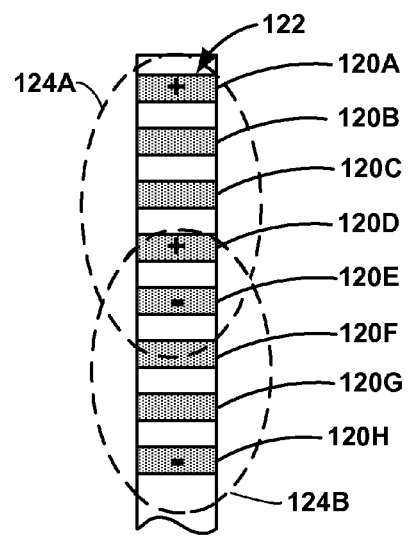
FIG. 10A    FIG. 10B
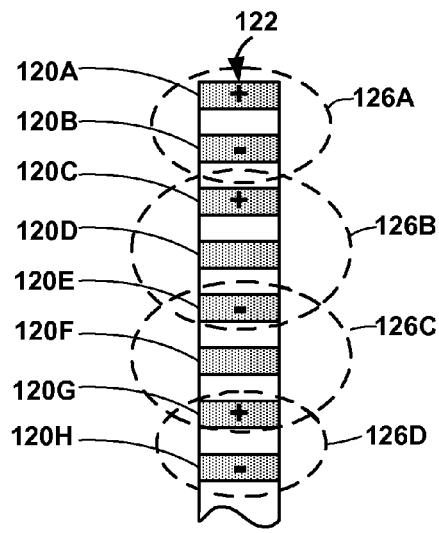
FIG. 10C

THERAPY PROGRAM MODIFICATION BASED ON AN ENERGY THRESHOLD

This application is a continuation of U.S. patent application Ser. No. 12/989,726, entitled, "THERAPY PROGRAM MODIFICATION BASED ON AN ENERGY THRESHOLD," which was filed Oct. 26, 2010, was issued as U.S. Pat. No. 8,548,596 on Oct. 1, 2013, and is a U.S. National Stage filing under 35 U.S.C. §371 of PCT Application No. PCT/US09/031,967, filed Jan. 26, 2009, which claims the benefit of U.S. Provisional Patent Application No. 61/048,774, filed Apr. 29, 2008, the disclosures of all of the above applications are referenced herein in their entirety.

TECHNICAL FIELD

The disclosure relates to medical devices, and, more particularly, to delivery of electrical stimulation by a medical device.

BACKGROUND

Implantable medical devices, such as electrical stimulators or therapeutic agent delivery devices, may be used to deliver electrical stimulation therapy to patients to treat a variety of symptoms or conditions such as chronic pain, tremor, Parkinson's disease, epilepsy, urinary or fecal incontinence, sexual dysfunction, obesity, mood disorders (e.g., depression), other psychiatric disorders (e.g., obsessive-compulsive disorder), gastroparesis or diabetes. In some cases, the electrical stimulation may be used to stimulate muscles, e.g., functional electrical stimulation (FES) to promote muscle movement or prevent atrophy. In the case of an electrical stimulation therapy system, an implantable medical device may deliver electrical stimulation therapy via one or more leads that include electrodes located proximate to a target tissue site, which may be proximate to the spinal cord, pelvic nerves, peripheral nerves, the stomach or other gastrointestinal organs or within the brain of a patient. Alternatively, electrical stimulation may be delivered by one or more electrodes associated with a leadless stimulator.

During a programming session, which may occur during implant of the medical device, during a trial session, or during a follow-up session after the medical device is implanted in the patient, a clinician may select therapy parameter values for the medical device that provide efficacious therapy to the patient. In the case of electrical stimulation delivered in the form of pulses, the therapy parameters may include an electrode combination (i.e., particular electrodes selected from an array of electrodes and the polarities of the selected electrodes), an amplitude, which may be a current or voltage amplitude, a pulse width, and a pulse rate for stimulation signals. In some cases, such as in current-based electrical stimulation systems, electrodes may be identified as source or sink electrodes. A group of therapy parameter values may be referred to as a program in the sense that they drive the stimulation therapy to be delivered to the patient.

SUMMARY

In general, the disclosure is directed to modifying a therapy program based on a comparison between an energy associated with the therapy program and an energy threshold value. In some examples, the therapy program may be modified in order to increase an energy efficiency of a medical device that delivers therapy according to the therapy program. In one example, an electrical stimulation signal defined by the therapy program is decomposed into a plurality of subsignals based on a comparison between an energy associated with the stimulation signal and a threshold value. For example, an electrical stimulation signal defined by a therapy program may be decomposed into a plurality of subsignals when an electrical stimulation energy of the stimulation signal exceeds the maximum energy output of the medical device or of a channel of the medical device. The energy associated with each one of the plurality of subsignals may be less than the energy of the stimulation signal.

In some examples, an original electrical stimulation signal may be decomposed into a plurality of subsignals while substantially maintaining the same physiological effects on the patient as the original stimulation signal. For example, the plurality of subsignals may define a signal envelope that substantially conforms to a signal envelope of the original electrical stimulation signal. A signal envelope may generally define the amplitude and pulse width parameters of the electrical stimulation. It is believed that in some cases, the subsignals may be spatially separated, e.g., by about 1 millisecond or less, while generally maintaining the physiological effects of the original stimulation signal due to the carry-over effect. A carry-over effect generally refers to a physiological effect from an electrical stimulation signal that persists after termination of the signal. In some examples, a medical device decomposes an original electrical stimulation signal into a plurality of subsignals that are separated by a time duration that is less than the duration of the carry-over effect, such that the patient does not perceive the delivery of the separate subsignals, and such that the therapeutic effect of the subsignals is substantially equal to that of the original electrical stimulation signal.

In some examples, a therapy program may be modified to increase an energy efficiency of a medical device by decomposing a therapy field that defines an area of tissue to which therapy is delivered into a plurality of therapy subfields, while substantially maintaining the same physiological effects as the original therapy field. For example, a volume of an aggregate therapy field defined by overlapping the plurality of therapy subfields may substantially equal or be within a particular percentage (e.g., 10%) of a total volume of the original therapy field. A therapy field may be decomposed into a plurality of therapy subfields by generating a plurality of therapy subprograms that are each associated with one of the subfields. In one example, the medical device may deliver stimulation according to the therapy programs to generate the therapy subfields in a substantially sequential manner, such that the time at which therapy is delivered according to subsequent therapy programs is separated by a time duration that is less than the duration of the carry-over effect. In this way, the therapeutic effect of therapy delivery according to a plurality of therapy subfields is substantially equal to the therapeutic effect of therapy delivery according to the original therapy field.

In one aspect, the disclosure describes a method comprising receiving information that defines a therapy program, where the therapy program comprises at least one stimulation parameter value defining a stimulation signal. The method further comprises comparing an energy associated with the stimulation signal to a threshold value, and modifying the therapy program to decompose the stimulation signal into a plurality of subsignals based on the comparison between the energy associated with the stimulation signal and the threshold value.

In another example, the disclosure describes a system comprising a memory that stores a therapy program comprising at least one stimulation parameter defining a stimulation signal, and a processor that determines a first energy associated with the stimulation signal, compares the first energy to a threshold value, and modifies the therapy program to decompose the stimulation signal of the therapy program into a plurality of subsignals based on the comparison between the energy and the threshold value. A second energy associated with each of the plurality of subsignals is less than the first energy associated with the stimulation signal In another example, the disclosure describes a computer-readable medium comprising instructions that cause a processor to receive information that defines a therapy program, which comprises at least one stimulation parameter defining a stimulation signal. The computer-readable medium includes further instructions to cause the processor to compare an energy associated with the stimulation signal to a threshold value, and modify the therapy program to decompose the stimulation signal into a plurality of subsignals based on the comparison between the energy associated with the stimulation signal and the threshold value.

In another example, the disclosure describes a system comprising means for receiving information that defines a therapy program, which comprises at least one stimulation parameter defining a stimulation signal. The system further comprises means for comparing an energy associated with the stimulation signal to a threshold value, and means for modifying the therapy program to decompose the stimulation signal into a plurality of subsignals based on the comparison between the energy associated with the stimulation signal and the threshold value.

In another example, the disclosure describes a method comprising receiving information that defines a therapy program, where therapy delivery to a patient by a medical device according to the therapy program generates a therapy field. The method further comprises comparing an energy associated with the therapy program to a threshold value, and generating a plurality of therapy subprograms to decompose the therapy field into a plurality of therapy subfields based on the comparison between the energy associated with the therapy program and the threshold value.

In another example, the disclosure describes a system that comprises a memory storing information that defines a therapy program. The therapy program comprising at least one stimulation parameter that defines a therapy field. The system further comprises a processor that determines an energy associated with the therapy program, compares the energy associated with the therapy program to a threshold value, and generates a plurality of subprograms that decompose the therapy field into a plurality of therapy subfields based on the comparison between the energy and the threshold value.

In another example, the disclosure describes a computer-readable medium comprising instructions that cause a processor receive information that defines a therapy program, where therapy delivery to a patient by a medical device according to the therapy program generates a therapy field. The instructions further cause the processor to compare an energy associated with the therapy program to a threshold value, and generate a plurality of therapy subprograms to decompose the therapy field into a plurality of therapy subfields based on the comparison between the energy associated with the therapy program and the threshold value.

In another example, the disclosure describes a system comprising means for receiving information that defines a therapy program, where therapy delivery to a patient by a medical device according to the therapy program generates a therapy field. The system further comprises means for comparing an energy associated with the therapy program to a threshold value, and means for generating a plurality of therapy subprograms to decompose the therapy field into a plurality of therapy subfields based on the comparison between the energy associated with the therapy program and the threshold value.

BRIEF DESCRIPTION OF DRAWINGS

FIGS. 3B-3D are example timing diagrams of stimulation subsignals that may be generated based on the electrical stimulation signals of FIG. 3A.

FIG. 10A is a diagram illustrating an example therapy field.

FIGS. 10B and 10C are diagrams illustrating example therapy subfields generated based on the therapy field of FIG. 10A.

DETAILED DESCRIPTION

Figure 1:
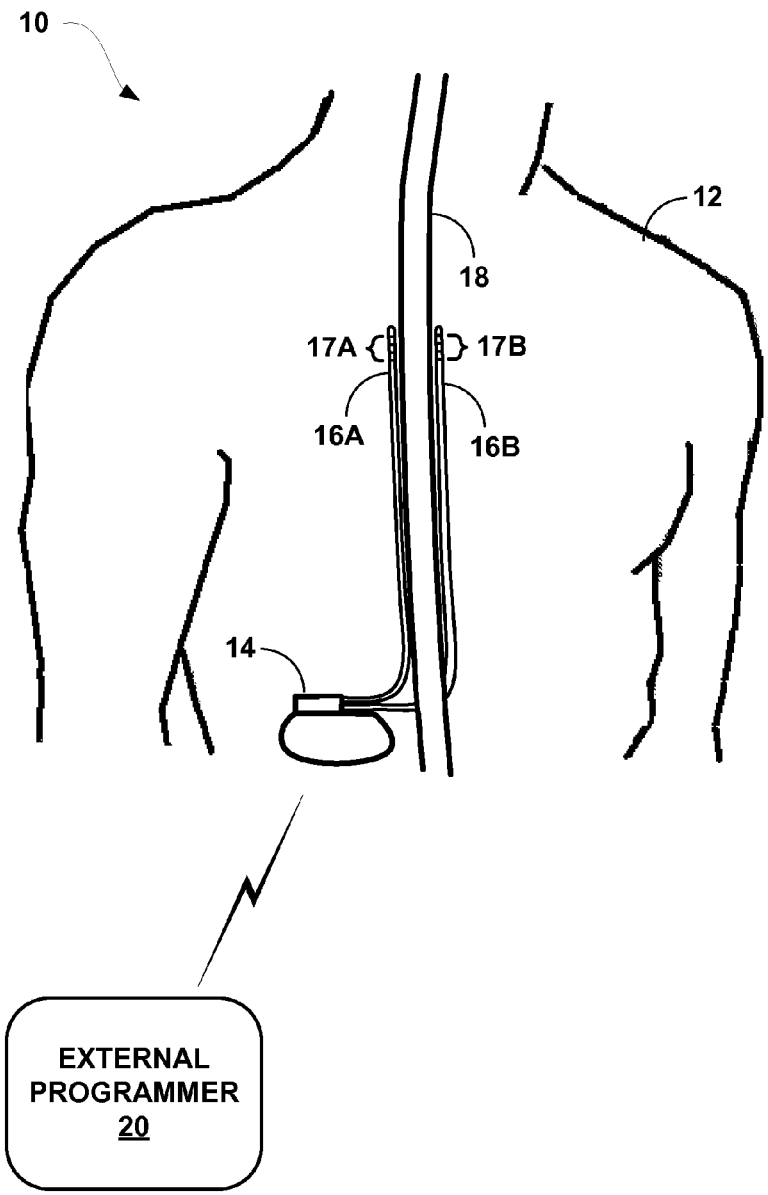
FIG. 1 is a schematic diagram illustrating an example implantable stimulation system.

FIG. 1 is a schematic diagram illustrating an example therapy system 10, which includes an implantable medical device (IMD) 14 and medical leads 16A, 16B (collectively "leads 16"). Leads 16 each include a plurality of electrodes 17A, 17B, respectively. In the example shown in FIG. 1, IMD 14 and leads 16 are implanted within a patient 12. Patient 12 will ordinarily be a human patient. In some cases, however, the systems, methods, and techniques described herein may be applied to non-human patients.

As shown in FIG. 1, system 10 may also include a programmer 20, which may be a handheld device, portable computer, or workstation that provides a user interface to a clinician. The clinician may interact with the user interface to program stimulation parameters for IMD 14, which may include, for example, the electrodes 17A, 17B (collectively "electrodes 17") that are selected to deliver electrical stimulation to patient 12, the polarity of the selected electrodes, and a current or voltage amplitude, and, in the case of stimulation pulses, a pulse width and pulse rate (or frequency) of the stimulation signals to be delivered to patient 12. The stimulation parameters may be arranged into therapy programs, where each program sets forth an electrode combination (i.e., the selected electrodes and respective polarities), current or voltage amplitude, and, in the case of stimulation pulses, the pulse width and pulse rate for therapy delivery.

Electrodes 17 are electrically coupled to a stimulation generator within IMD 14 via one or more conductors of leads 16. Electrodes 17 may be electrode pads, circular (i.e., ring) electrodes surrounding the body of leads 16, partial-ring electrodes, segmented electrodes, conformable electrodes, cuff electrodes, or any other type of electrodes capable of forming unipolar, bipolar or multipolar electrode configurations. In the example of FIG. 1, electrical stimulation is delivered from IMD 14 to a target tissue site proximate to spinal cord 18 of patient 12 via one or more electrodes 17 carried by axial leads 16 implanted within patient 12. For example, leads 16 may be implanted within patient 12 such that electrodes 17 are positioned external to the spinal cord 18 dura layer or within the epidural space of spinal cord 18. Various combinations of electrodes 17 carried by the leads 16 may be used to deliver electrical stimulation to the target tissue site within patient, including combinations of electrodes on a single lead 16A or 16B, or combinations of electrodes on both leads 16. Also, in some examples, electrodes may be carried by one or more paddle leads in addition to or instead of leads 16. A paddle lead may include an array of electrodes that are arranged in a two-dimensional pattern, e.g., as columns or rows of electrodes.

Spinal cord stimulation (SCS), which is shown in FIG. 1, may be used to eliminate or reduce pain perceived by patient 12, or for other therapeutic purposes. However, in other examples, IMD 14 may be configured for use with a variety of different therapies, such as peripheral nerve stimulation (PNS), peripheral nerve field stimulation (PNFS), deep brain stimulation (DBS), cortical stimulation (CS), pelvic floor stimulation, gastric stimulation, muscle stimulation (e.g., functional electrical stimulation (FES) of muscles) and the like. The stimulation may be configured to alleviate a variety of symptoms or conditions such as, but not limited to, chronic pain, migraines, tremor, Parkinson's disease, sleep apnea, epilepsy, other movement disorders or seizure disorders, urinary or fecal incontinence, sexual dysfunction, obesity, gastroparesis, mood disorders or other psychiatric disorders. Accordingly, although patient 12 and SCS are referenced throughout the remainder of the disclosure for purposes of illustration, an electrical stimulation system 10 may be adapted for use in a variety of electrical stimulation applications.

IMD 14 may be implanted within patient 12, as shown in FIG. 1, or may be carried external to patient 12 and coupled to implanted leads via a percutaneous extension. For SCS applications, IMD 14 may be located, for example, in the lower abdomen, lower back, or other location to secure IMD 14. In some examples, leads 16 are tunneled from IMD 14 through tissue to reach the target tissue adjacent to spinal cord 18 for stimulation delivery.

Electrical stimulation generated and delivered by IMD 14 may take the form of stimulation pulses or continuous waveforms, and may be characterized by controlled voltage levels or controlled current levels. In the case of electrical stimulation by stimulation pulses, the stimulation signals may also be characterized by a pulse width and pulse rate. Although the disclosure primarily refers to electrical stimulation pulses, the techniques described herein for modifying a therapy program may also be applied to therapy programs that define continuous waveform electrical stimulation signals (e.g., sine waves).

During the course of therapy, whether the therapy is implemented on a chronic (i.e., less than temporary) or trial basis, IMD 14 may generate and deliver stimulation signals that are defined by a therapy program. Each stimulation signal delivered by IMD 14 to a target tissue site within patient 12 via leads 16 is associated with an energy, which may be the product of the power required to generate the stimulation signal and the duration of the stimulation signal, such as the pulse width in the case of stimulation pulses. The product of the power required to generate the stimulation signal and the duration of the stimulation signal may be represented by the notation W-seconds.

The power required to generate the stimulation signal is a product of the voltage and current needed to generate the stimulation signal. Therefore, an energy associated with a stimulation signal is a direct function of voltage, current, and duration of the stimulation signal. For ease of description, as used in the disclosure, however, the energy associated with an electrical stimulation signal may be considered to be a product of the amplitude and duration (e.g., pulse width) of the electrical signal. As described above, the amplitude of a stimulation signal may be a voltage or current amplitude. While the product of the amplitude and duration of a stimulation signal does not directly translate into energy, either the voltage amplitude or the current amplitude for a particular stimulation signal may be considered to be substantially constant for a given stimulation signal. Thus, the product of either the voltage or current amplitude and the duration of the stimulation signal is directly related to the energy associated with the stimulation signal.

As the product of the pulse width and either the voltage or current amplitude of a stimulation signal increases, the amount of energy required for IMD 14 to generate the stimulation signal increases. As previously indicated, the pulse width of the stimulation signal is a parameter of the therapy program that defines the duration of the stimulation signal. The pulse width may be considered to be an "on-time," during which IMD 14 delivers stimulation to patient 12. In examples in which the stimulation signal is a pulse, an amount of time between each pulse may be referred to as the interval between signals. The interval between signals may be considered to be an off-time, during which no stimulation is delivered to patient 12. In examples in which the stimulation signal is a continuous waveform, the stimulation energy of the continuous waveform may be a function of the requested interval of the continuous waveform and amplitude of the signal.

In some cases, IMD 14 has a limited energy output, i.e., a maximum energy output. The maximum energy output of IMD 14 may be the overall maximum energy output of IMD 14 or the maximum energy output one or more of the channels of IMD 14 (if IMD 14 has multiple channels). If IMD 14 is a multichannel device, IMD 14 may be capable of delivering electrical stimulation signals to patient 12 through multiple channels. In some cases, IMD 14 may be incapable of generating stimulation signals having an energy greater than or equal to a threshold value, which may be substantially equal to the maximum energy output of IMD 14 or for one or more of the channels of IMD 14. In other cases, IMD 14 may be capable of generating a stimulation signal having an energy greater than or equal to an energy threshold value, but it may be undesirable for IMD 14 to provide such a stimulation signal for purposes of energy efficiency of therapy system 10, e.g., in order to help extend the life of the power source within IMD 14. Thus, the energy threshold value may be, but need not be, substantially equal to a maximum energy output for IMD 14 or a channel thereof. In some examples, the energy threshold may be a predetermined or user configured value, which may be a function, e.g., fraction or percentage, of a maximum energy output for IMD 14 or a channel thereof.

In some cases, the amount of energy output that IMD 14 is capable of providing changes over time as the energy of a battery or other power source of IMD 14 depletes. In some cases, as a power source discharges, the power source may begin providing a lower voltage output. Therefore, in some examples, the energy threshold value (e.g., energy threshold value 36 shown in FIG. 2) may be dynamic, and may change over time based on a change in the amount of energy output that IMD 14 can provide. Additionally, in some examples, the energy threshold value may be based on a prediction of the amount of energy output that IMD 14 can provide in the future, based on past usage of the power source of IMD 14. For example, the energy threshold value may be set as at the minimum value of the maximum energy output of IMD 14 over the useful life of IMD 14, which may be, for example, an average of the maximum energy output of IMD 14 when the power source is at the maximum level, and the expected level of the power source at the end of the useful life of IMD 14. As another example, the energy threshold value may be set at the expected minimum energy output of the power source at the end of some period of time, such as about two years to about five years, e.g. about three years.

The energy threshold value for IMD 14 may be different in different examples, and may be determined by the manufacturer or distributor of IMD 14, by a clinician or another qualified individual or entity.

In some cases, a clinician generates a therapy program that defines a stimulation signal that has an energy that exceeds the energy threshold value of IMD 14. For example, a clinician may determine that a stimulation signal that is associated with an energy that exceeds the energy threshold provides the most effective therapy for the patient's condition. As another example, the clinician may select an efficacious therapy program for patient 12 with the aid of a trial stimulation device, which may have a greater energy threshold value than the chronic IMD 14. A therapy program may be determined to be effective based on the therapeutic results provided to patient 12 from therapy delivery according to the therapy program, a minimization of the side effects from therapy delivery according to the therapy program, or a combination thereof. Accordingly, when the clinician programs IMD 14 with the selected therapy program, the stimulation signal defined by the therapy program may have an energy (or may be associated with an energy) that exceeds the threshold energy value.

IMD 14 may decompose a stimulation signal defined by a therapy program into a plurality of subsignals, where an energy associated with each one of the plurality of subsignals is less than the energy associated with the stimulation signal. This may be useful for situations in which a therapy program defines a stimulation signal that is associated with an energy that exceeds a threshold energy value for IMD 14. Each signal of the plurality of subsignals may be temporally separated by an interval of time, i.e., an "off-time." In some examples, the time interval between subsignals may be less than the duration of a carry-over effect generated by the delivery of the subsignal. A carry-over effect generally refers to a physiological effect from an electrical stimulation signal that persists after termination of the signal. The duration of the carry-over effect may be specific to patient 12 or may be generalized for more than one patient. The duration of the carry-over effect may be a value that is stored within IMD 14 or programmer 20.

By separating the subsignals by a time interval that is less than the duration of the carry-over effect, patient 12 does not feel a discontinuous therapeutic effect from the plurality of subsignals. The subsignals may be spatially separated, e.g., by about 1 millisecond or less, while generally maintaining the physiological effects of the original stimulation signal due to the carry-over effect. Alternatively, time interval between stimulation subsignals may be greater than the time of the carry-over effect. Techniques for decomposing a stimulation signal into a plurality of subsignals are described in more detail below with reference to FIGS. 3A-3D, 5, and 6.

In some examples, IMD 14 decomposes a stimulation signal defining a signal envelope into a plurality of subsignals that define a signal envelope that substantially conforms to the signal envelope of the stimulation signal. The substantially similar signal envelopes may help maintain the therapeutic effects of the therapy program, even though a stimulation signal defined by the therapy program is decomposed into plurality of subsignals.

A signal envelope may be defined by the amplitude and duration of the stimulation signal. In the case of a stimulation pulse, the duration of the stimulation signal is the pulse width of the stimulation signal. The plurality of subsignals may define a signal envelope that mimics the outer boundaries of the signal envelope of the stimulation signal. For example, if the original stimulation signal has a duration of X, each of the subsignals may not have the same duration X, but the sum of the duration of the subsignals, including any time intervals between the subsignals, may substantially equal X. Signal envelopes are described in further detail below with respect to FIGS. 3A-3D. In other examples, the plurality of subsignals may define a signal envelope that differs from the signal envelope of the stimulation signal.

With reference to FIG. 1, a user, such as a clinician, physician or patient 12, may interact with a user interface of external programmer 20 to program IMD 14. Programmer 20 is an external computing device that is configured to wirelessly communicate with IMD 14. For example, programmer 20 may be a clinician programmer that the clinician uses to communicate with IMD 14. Alternatively, programmer 20 may be a patient programmer that allows patient 12 to view and modify therapy parameters. The clinician programmer may include more programming features than the patient programmer. In other words, more complex or sensitive tasks may only be allowed by the clinician programmer to prevent patient 12 from making undesired changes to IMD 14.

Programming of IMD 14 may refer generally to the generation and transfer of commands, programs, or other information to control the operation of IMD 14. For example, programmer 20 may transmit programs, parameter adjustments, program selections, group selections, or other information to control the operation of IMD 14, e.g., by wireless telemetry. Parameter adjustments may refer to initial parameter settings or adjustments to such settings. A program may specify a set of parameters that define stimulation. A group may specify a set of programs that define different types of stimulation, which may be delivered simultaneously using pulses with independent amplitudes or on a time-interleaved basis.

Programmer 20 may be a hand-held computing device that includes a display viewable by the user (e.g., a clinician or patient 12) and a user input mechanism that can be used to provide input to programmer 20. For example, programmer 20 may include a small display screen (e.g., a liquid crystal display or a light emitting diode display) that presents information to the user. In addition, programmer 20 may include a keypad, buttons, a peripheral pointing device, touch screen or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone or personal digital assistant that is configured to run an application that simulates one or more functions of programmer 20. Alternatively, a notebook computer, tablet computer, or other personal computer may run an application that enables the computer to function as programmer 20. A wireless adapter may be connected to the personal computer to enable to computer to securely communicate with IMD 14.

When programmer 20 is configured for use by the clinician, programmer 20 may be used to transmit initial programming information to IMD 14. This initial information may include hardware information of therapy system 10, such as the type of lead 16, the position of lead 16 within patient 12, the therapy parameters of therapy programs stored within IMD 14 or within programmer 20, the energy threshold value for a stimulation signal generated and delivered by IMD 14, and any other information the clinician desires to program into IMD 14.

With the aid of programmer 20 or another computing device, a clinician may select therapy parameter values for therapy system 10, where a group of therapy parameter values may be stored as a therapy program. In examples, each therapy program defines an electrode combination, and respective values for a voltage or current amplitude, pulse rate (or frequency), and pulse rate. By selecting particular electrode combinations, a clinician may target particular tissue sites proximate to spinal cord 18. In addition, by selecting values for amplitude, pulse width, and pulse rate, the clinician may generate an efficacious therapy for patient 12 that is delivered via the selected electrode subset. Due to physiological diversity, condition differences, and in accuracies in lead placement, the parameters may vary between patients.

During a programming session, the clinician may determine one or more therapy programs that result in efficacious therapy to patient 12. Patient 12 may provide feedback to the clinician as to the efficacy of the specific program being evaluated or the efficacy feedback may be provided by one or more physiological sensors that sense physiological parameters that are indicative of the efficacy of therapy. In some examples, programmer 20 may assist the clinician in the creation/identification of therapy programs by providing guidance during programming and/or some methodical system for identifying and testing potentially beneficial therapy parameters.

Programmer 20 may also be configured for use by patient 12. When configured as the patient programmer, programmer 20 may have limited functionality in order to prevent patient 12 from altering critical functions or applications that may be detrimental to patient 12. In this manner, programmer 20 may only allow patient 12 to adjust certain therapy parameters or set an available range for a particular therapy parameter. Programmer 20 may also provide an indication to patient 12 when therapy is being delivered or when IMD 14 or when the power source within programmer 20 or IMD 14 need to be replaced or recharged.

Whether programmer 20 is configured for clinician or patient use, programmer 20 may communicate to IMD 14 or any other computing device via wireless communication. Programmer 20, for example, may communicate via wireless communication with IMD 14 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 14 and other another programmer via remote telemetry techniques known in the art, communicating via a local area network (LAN), wide area network (WAN), public switched telephone network (PSTN), or cellular telephone network, for example.

An example of a commercially available clinician programmer is the Medtronic N'Vision® Programmer Model 8840, marketed by Medtronic, Inc., of Minneapolis, Minn. An example of a commercially available patient programmer is the Medtronic myStim® Programmer, marketed by Medtronic, Inc.

Although FIG. 1 illustrates a system 10 that includes an implantable IMD 14 coupled to fully implanted leads 16A, 16B, the techniques described in this disclosure may be applied to systems including external stimulators coupled to leads via percutaneous lead extensions, leadless stimulators (e.g., microstimulators), and the like. A leadless stimulator may carry an array of electrodes, e.g., rows, columns, or other patterns of electrodes. For leads 16A, 16B or other electrode arrays, electrodes may be formed as any of a variety of electrodes such as ring electrodes, segmented electrodes, partial-ring electrodes, surface electrodes, needle electrodes, pad electrodes, or the like. In general, the term "electrode array" may refer to electrodes deployed on a lead comprising a substantially cylindrical cross section at a distal portion, referred to herein as an axial lead, or may refer to electrode deployed on paddle leads, other lead configurations, or in leadless arrangements.

Figure 2:
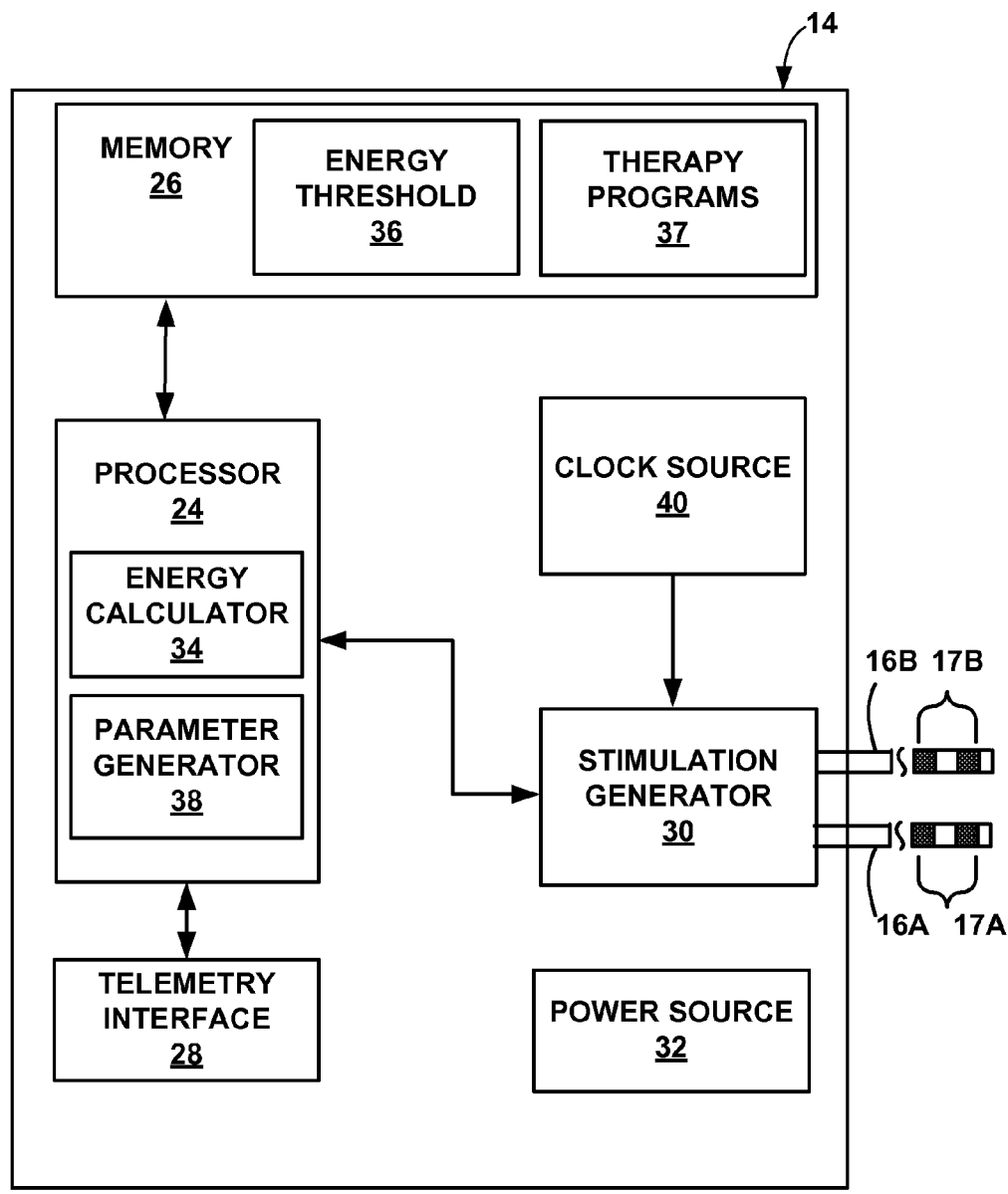
FIG. 2 is a functional block diagram illustrating an example implantable stimulator.

FIG. 2 is a functional block diagram illustrating various components of an example IMD 14. In the example of FIG. 2, IMD 14 includes processor 24, memory 26, telemetry interface 28, stimulation signal generator 30, and power source 32. Memory 26 may include computer-readable instructions that, when executed by processor 24, cause IMD 14 to perform various functions. Memory 26 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 26 may store instructions for execution by processor 24, stimulation therapy program data, sensor data (if applicable), operational and status data of IMD 14 and patient 12, and any other information regarding therapy or patient 12. Stimulation program data may include stimulation parameters transmitted from programmer 20, as well as programs defined by such parameters, and program groups. Some data may be recorded for long-term storage and retrieval by a user. Memory 26 may include separate memories for storing different types of data.

Memory 26 also stores an energy threshold value 36, which may be the maximum energy output value of IMD 14 or a channel of IMD 14, and therapy programs 37. As previously indicated, each of therapy programs 37 may specify values for a set of parameters for delivery of electrical stimulation therapy, such as an electrode combination, electrode polarities, current or voltage amplitude, pulse rate, and pulse width. Additional parameters such as duty cycle, duration, and delivery schedule also may be specified by a therapy program.

Processor 24 may be provided by one or more microprocessors, digital signal processors (DSPs), application specific integrated circuits (ASICs), field programmable gate arrays (FPGAs), any other equivalent integrated or discrete logic circuitry. Functions attributed to processor 24 herein may be embodied as hardware, firmware, software, or any combination thereof. Upon selection of one of therapy programs 37 or a group of therapy programs 37 (e.g., a group that includes more than one therapy program) from memory 26, processor 24 may control stimulation generator 30 to generate and deliver stimulation according to the programs in the group, e.g., simultaneously or on a time-interleaved basis. A group may include a single program or multiple programs, each of which specifies an electrode combination. For example, under the control of processor 24, stimulation generator 30 may deliver electrical stimulation therapy via electrodes 17A, 17B of one or more leads 16, e.g., as stimulation pulses or continuous waveforms.

Stimulation generator 30 may include stimulation generation circuitry to generate stimulation pulses or waveforms and switching circuitry to switch the stimulation across different electrode combinations, e.g., in response to control by processor 24. Processor 24 may control the switching circuitry on a selective basis to cause stimulation generator 30 to deliver electrical stimulation to selected combinations of electrodes 17A, 17B and to shift the electrical stimulation to different electrode combinations. In some examples, stimulation generator 30 includes multiple current or voltage sources to control delivery of stimulation energy to selected combinations of electrodes 17A, 17B carried by leads 16.

Using an external programmer, such as programmer 20, a user may select individual programs for delivery on an individual basis, or combinations of programs (e.g., groups of therapy programs) for delivery on a simultaneous or interleaved basis. In addition, a user may adjust parameters associated with the programs. The programs may be stored in memory 26 of implantable IMD 14, as shown in FIG. 2. Alternatively, the programs may be stored in memory associated with external programmer 20 or another external device. In either case, the programs may be selectable and adjustable to permit modification of therapy parameters. In addition, programmer 20 may permit generation of new programs, which may be loaded into memory 26, and adjustment of parameters associated with existing programs.

IMD 14 may be responsive to the adjustment of programming parameters and electrode configurations by a user via programmer 20. In particular, processor 24 may receive adjustments to parameters of stored therapy programs 37 or receive new therapy programs from programmer 20 via telemetry interface 28. Telemetry interface 28 supports wireless telemetry with external programmer 20 or another device by radio frequency (RF) communication, proximal inductive interaction of IMD 14 with external programmer 20, or other techniques. Telemetry interface 28 may send information to and receive information from external programmer 20 on a continuous basis, at periodic intervals, or upon request from IMD 14 or programmer 20. To support RF communication, telemetry interface 28 may include appropriate electronic components, such as amplifiers, filters, mixers, encoders, decoders, modulators, demodulators, and the like.

Power source 32 delivers operating power to the components of IMD 14. Power source 32 may include a small rechargeable or non-rechargeable battery and a power generation circuit to produce the operating power. In examples in which power source 32 is rechargeable, recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional nonrechargeable batteries may be used for a limited period of time. As a further alternative, an external inductive power supply could transcutaneously power IMD 14 when needed or desired.

IMD 14 may also include energy calculator 34, parameter generator 38, and clock source 40. Though clock source 40 is shown as a separate component in the functional block diagram of FIG. 2, in some examples, parameter generator 38 may include clock source 40. Moreover, although energy calculator 34 and parameter generator 38 are shown to be a part of processor 24, in other examples, energy calculator 34 and stimulation parameter generator 38 may be a part of separate processors, may be firmware or software executed by separate processors.

Energy calculator 34 may be provided by one or more microprocessors, DSPs, ASICs, FPGAs, any other equivalent integrated or discrete logic circuitry, and may be embodied as hardware, firmware, software, or any combination thereof. Energy calculator 34 determines the energy of a therapy program based on the pulse width and amplitude of the stimulation signal defined by the parameter values of the therapy program. The therapy program may be selected from therapy programs 37 stored in memory 26, or the therapy program may be transmitted to IMD 14 by external programmer 20.

Processor 24 may compare the determined energy of the selected therapy program to the energy threshold value 36. For example, upon receiving information indicative of a selected therapy program, e.g., via programmer 20 or by selecting a therapy program from memory 26 of IMD 14, processor 24 may control energy calculator 34 to determine an energy associated with the stimulation signal defined by the selected therapy program. Energy calculator 34 may determine the energy associated with the stimulation signal by, for example, multiplying the amplitude of the signal with the duration parameter value (e.g., the pulse width) of the stimulation signal. Upon determining the energy of the stimulation signal, processor 24 may compare the determined energy level with the energy threshold value 36 of IMD 14, which may be the maximum energy output of IMD 14, the maximum energy output of a channel of IMD 14 or the maximum desirable energy output of IMD 14.

In some examples, stimulation parameter generator 38 decomposes the stimulation signal defined by the therapy program based on a comparison between the energy associated with the stimulation signal and energy threshold value 36. For example, if the energy associated with the stimulation signal is greater than energy threshold value 36, processor 24 may control stimulation parameter generator 38 to generate a plurality of stimulation subsignals based on the stimulation signal. Alternatively, processor 24 may control stimulation parameter generator 38 to generate a plurality of stimulation subsignals if the energy associated with the stimulation signal is greater than or equal to the threshold value 36. An energy associated with each of the subsignals may be less or equal to the energy of associated with the stimulation signal. In some cases, the energy associated with each one of the plurality of subsignals is less than energy threshold value 36. Furthermore, in some examples, a total energy of the subsignals may be less than, equal to or greater than an energy associated with the stimulation signal.

On the other hand, if processor 24 determines that the energy of the stimulation signal defined by a therapy program and determined by energy calculator 34 is less than energy threshold value 36, parameter generator 38 may not subdivide the signals into subsignals, and processor 24 may control stimulation generator 30 to deliver therapy to patient 12 in accordance with the original stimulation signal defined by the therapy program. In some examples, however, parameter generator 38 may subdivide the signals into a plurality of subsignals even though the energy of the stimulation signal of the received therapy program is less than the energy threshold value 36. This may help, for example, conserve power source 32.

If the energy of the stimulation signal defined by the selected therapy program exceeds (e.g., is greater than) or is equal to energy threshold value 36, parameter generator 38 may modify the therapy program to decompose the stimulation signal into a plurality of subsignals. In one example, stimulation parameter generator 38 modifies the parameter values of the therapy program defining the stimulation signal in order to generate the stimulation parameter values for each subsignal. Stimulation parameter generator 38 may define the pulse width for the plurality of subsignals and the interval of time between subsignals, i.e., the time between subsignals during which IMD 14 is not providing stimulation to the target tissue. Example techniques that may be implemented by stimulation parameter generator 38 to create parameter values based on the received therapy program are described below with reference to FIGS. 3A-3D, 4, and 5.

FIGS. 3A-3D are schematic timing diagrams illustrating example techniques for decomposing a stimulation signal into a plurality of subsignals, where each of the subsignals has an energy that is less than an energy of the stimulation signal. That is, the energy required to generate each of the subsignals is less than the energy required to generate the stimulation signal.

Figure 3A:
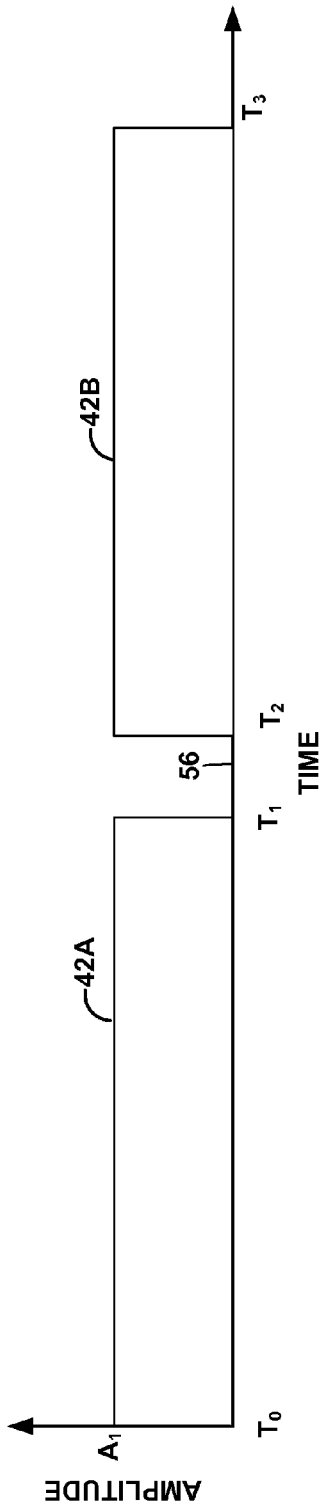
FIG. 3A is an example timing diagram of electrical stimulation signals defined by a therapy program.

FIG. 3A is a timing diagram illustrating electrical stimulation signals 42A and 42B (collectively referred to as "stimulation signals 42") defined by a therapy program. The therapy program may be, for example, a therapy program determined to provide efficacious therapy to patient 12. The therapy program may be selected by patient 12, clinician or processor 24 (e.g., from memory 26) for delivery of stimulation therapy to patient 12. In the example shown in FIG. 3A, the signals 42 each define stimulation pulses. Although two signals 42A, 42B are shown in FIG. 3A, the therapy program may define a plurality of pulses 42 in an indefinite or definite pulse train.

FIG. 3A illustrates a time interval 56 between stimulation pulses 42A, 42B. The length of interval 56 is a function of the frequency or pulse rate of the pulses 42 defined by the therapy program, as well as the pulse width of each pulse 42A, 42B. That is, the frequency of pulses 42 defined by the therapy program may be an inverse of the sum of the pulse width and the time interval 56 between pulses 42A, 42B. In FIG. 3A, interval 56 is the difference between time $T_2$, at which the second pulse 42B begins, and time T1, at which the first pulse 42A terminates. The duration (or pulse width) of stimulation pulses 42A, 42B is approximately the same. In other examples, however, stimulation pulses 42A, 42B may have different durations. Each pulse 42A, 42B defines a stimulation envelope 45 (shown in FIG. 3B), which represents the general amplitude and duration of the stimulation signal that has been determined to provide efficacious therapy to patient 12.

Prior to delivering therapy to patient 12 according to the selected therapy program, energy calculator 34 (e.g., under the control of processor 24) may determine the energy of each of the stimulation signals 42 defined by the therapy program. As previously described, in some cases, the energy is generally be determined by multiplying the amplitude $A_1$ of one of the stimulation signals 42 by the respective duration ($T_1$ or $T_3-T_2$) of the respective electrical stimulation signal 42. Processor 24 may compare the determined energy of one of the stimulation signals 42 defined by the current therapy program to the energy threshold value 36 (FIG. 2) stored in memory 26. In the example of FIG. 3A, the energy of each of the stimulation signals 42 is greater than the energy threshold value 36. Accordingly, stimulation parameter generator 38 may decompose each of the signals 42 into a plurality of subsignals that each have an energy lower than one of the signals 42, and, in some cases, lower than the energy threshold value 36.

Figure 3B:
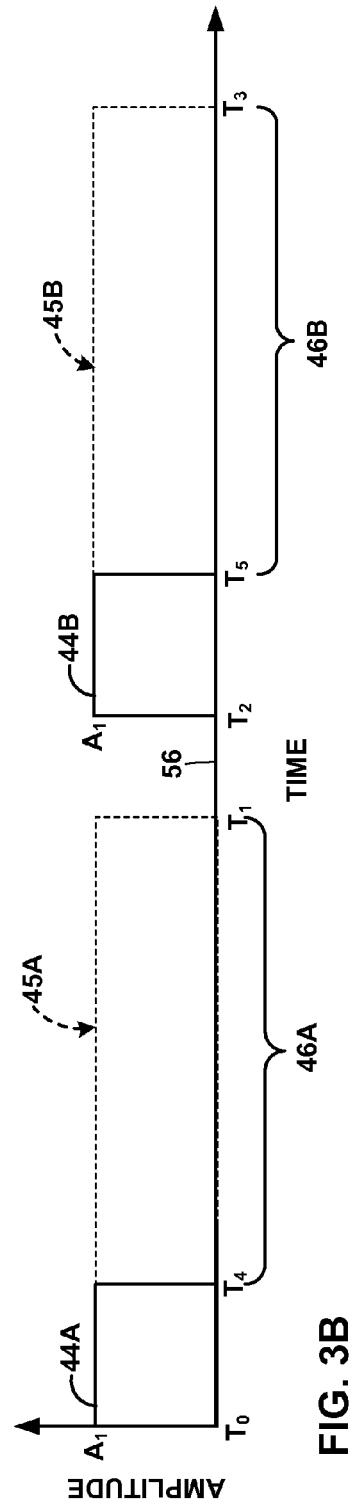

FIG. 3B illustrates a schematic timing diagram of a subsignals 44A, 44B (collectively referred to as "subsignals 44") that may be generated by stimulation parameter generator 38 based on signals 42, respectively. Stimulation parameter generator 38 may assign the amplitude $A_1$ of the stimulation signals 42 defined by the therapy program (the "original" stimulation signal) to each of the subsignals 44. In order to reduce the energy associated with each of the subsignals 44, however, parameter generator 38 may decrease the duration (i.e., pulse width in the case of electrical stimulation pulses) of the subsignals 44 compared to signals 42. For example, with respect to stimulation signal 42A having a duration $T_1$, a duration of a subsignal 44A generated based on signal 42A may be decreased to $T_4$. Accordingly, stimulation subsignal 44A has a pulse width $T_4$, which is less than the pulse width $T_1$ of signal 42A. In the example shown in FIG. 3B, pulse width $T_4$ may denote the maximum pulse width at which subsignal 44A with amplitude $A_1$ has an energy substantially equal to or less than the energy threshold value 36.

In examples in which the difference between time $T_4$, at which the subsignal 44A ends, and the time $T_1$, which indicates the pulse width of original stimulation signal 42A, is substantially equal to or less than the duration of a carry-over effect generated by delivery of stimulation subsignal 44A to patient 12, parameter generator 38 may not decompose original stimulation signal 42A into a plurality of subsignals. Instead, a single subsignal 44A may provide efficacious therapy in place of original stimulation signal 42A. As a result, the subsignal 44A generated based on original signal 42A may not maintain the same signal envelope 45A defined by the original stimulation signal 42A. Although signal envelope 45A may generally represent a signal that provides efficacious therapy to patient 12, in the case of subsignal 44A, efficacious therapy may be achieved by the delivery of subsignal 44A in conjunction with the carry-over effect from the delivery of subsignal 44A.

Similarly, parameter generator 38 may also decrease the duration ($T_2-T_3$) of stimulation signal 42B in order to decompose stimulation signal 42B into a subsignal 44B with a lower energy. As shown in FIG. 3B, the duration of subsignal 44B is generally equal to time $T_5-T_2$. The duration of subsignal 44B may denote the maximum pulse width at which subsignal 44B with amplitude $A_1$ has an energy substantially equal to or less than the energy threshold value 36. Just as with the decomposition of subsignal 42A, in examples in which the difference between time $T_5$, at which the subsignal 44B ends, and the time $T_3$, which indicates the pulse width of original stimulation signal 42B, is substantially equal to or less than the duration of a carry-over effect generated by delivery of stimulation subsignal 44B to patient 12, parameter generator 38 may not decompose original stimulation signal 42B into a plurality of subsignals.

In order to substantially maintain the frequency between signals 42 defined by the therapy program, parameter generator 38 may also select an "off-time" 46A, 46B for each subsignal 44A, 44B, respectively, during which IMD 14 does not delivery therapy to patient 12. Off-time 46A may be substantially equal to the difference between times $T_1$ and $T_4$ (i.e., $T_1$–$T_4$), and off-time 46B may be substantially equal to the difference between times $T_3$ and $T_5$ (i.e., $T_3$–$T_5$). Off-time 46A may be combined with the original time interval 56 between stimulation signals 42A, 42B defined by the therapy program in order to substantially maintain the frequency of stimulation signals defined by the therapy program. A pulse rate parameter of stimulation signals 42 may be modified based on pulse width $T_4$ and off-times 46A, 46B. The pulse rate for subsignals 44A, 44B may be determined as the inverse of the sum of the pulse width $T_4$ and off-times 46A, 46B, respectively.

Parameter generator 38 may transmit the modified therapy parameters, e.g., modified pulse width $T_4$ and pulse rate of subsignals 44, or all of the therapy parameters, e.g., the amplitude $A_1$, modified pulse width $T_4$, and pulse rate for subsignal 44, as well as a time interval 56 between original stimulation signals 42, to processor 24, and processor 24 may control stimulation generator 30 to generate and deliver therapy according to a modified therapy program defining a stimulation pulse with pulse width $T_4$, and substantially similar amplitude $A_1$, pulse rate (i.e., frequency of signals 42 may be defined by the inverse of the sum of the pulse width $T_4$ and the off-time), and electrode combination as the selected therapy program. In some examples, parameter generator 38 may transmit modified pulse width $T_4$ to processor 24, which may itself be sufficient to indicate or define the change from the original therapy program defining stimulation signals 42 to a therapy program defining decomposed stimulation signals comprising respective subsignals 44. If desired, the modified therapy parameters may be stored within memory 26 as a therapy program 37, or with unmodified therapy parameters of the original program as a modified program 37.

Subsignals 44A, 44B are examples of one type of decomposed stimulation signal that provides efficacious therapy to patient 12. In other examples, stimulation parameter generator 38 may decompose each original signal 42A, 42B into more than one subsignal. FIG. 3C illustrates a schematic timing diagram that illustrates a plurality of subsignals 48A-48F (collectively referred to as "subsignals 48") and 49A-49B (collectively referred to as "subsignals 49") generated based on each original stimulation signal 42A, 42B (FIG. 3A).

Each of the subsignals 48, 49 has an energy or is otherwise associated with an energy that is lower than a total energy associated with original stimulation signals 42A or 42B, and, in some cases, each of the subsignals 48, 49 has an energy lower than the energy threshold value 36 of IMD 14. In addition, a total energy of the subsignals 48A-48C and 49A may be less than, equal to or greater than the energy associated with the original stimulation signal 42A, and a total energy of the subsignals 48D-48F and 49B may be less than, equal to or greater than the energy associated with the original stimulation signal 42B. In the latter case, in which a total energy of the subsignals 48, 49 is greater than the energy of stimulation signal 42A, 42B, respectively, it may be desirable to distribute the energy consumption of IMD 14 over time due to energy throughput limitations of IMD 14. For example, if it is undesirable for IMD 14 to deliver therapy to patient 14 with a therapy program that is associated with certain energy over a certain period of time, it may be desirable to decompose the stimulation signal defined by the therapy program into subsignals in order to break up the energy output requirements of IMD 14.

In the example shown in FIG. 3C, stimulation signal 42A is decomposed into three subsignals 48A-48C and one subsignal 49A, which defines a pulse train 51. Stimulation signal 42B is decomposed into a plurality of subsignals 48D-48F, 49B defining a substantially similar pulse train as subsignals 48A-C, 49A. In other examples, parameter generator 38 may generate any suitable number of subsignals based on each of the original stimulation signals 42 defined by the therapy program. The number of subsignals in each pulse train 51 may depend on various factors, such as, for example, the duration of the carry-over effect generated by delivery of a subsignal and the energy threshold value 36 of IMD 14. For example, in some cases, it may be desirable to decompose each of the original signals 42 into a plurality of subsignals, such that each subsignal is separated by a time interval less than or equal to the duration of the carry-over effect.

Parameter generator 38 may modify at least one parameter value of the selected therapy program to define subsignals 48, 49. In the example shown in FIG. 3C, parameter generator 38 maintains the amplitude $A_1$ of signals 42 for each of the subsignals 48, 49. In order to reduce the energy associated with each of the subsignals 48, 49, however, parameter generator 38 may decrease the duration (i.e., pulse width in the case of electrical stimulation pulses) $T_1$ and ($T_3$–$T_2$) of stimulation signals 42A, 42B, respectively (FIG. 3A). The pulse width of each of the subsignals 48, 49 may be selected to be less than or equal to the maximum permissible pulse width $T_4$ (FIG. 3B), which may be, for example, the maximum pulse width at which the energy of each of the subsignals 48, 49 having amplitude $A_1$ does not exceed the threshold energy value 36.

In FIG. 3C, the time interval between the end of subsignal 48A and the end of the pulse envelope 45A defined by original stimulation signal 42A (i.e., $T_1$–$T_5$) is greater than the duration of a carry-over effect that results from delivery of subsignal 48A having pulse width $T_5$ and amplitude $A_1$. Accordingly, parameter generator 38 may decompose each of the stimulation signals 42 into more than one subsignal in order to maintain the therapeutic effects of the stimulation delivery. For example, as shown in FIG. 3C, parameter generator 38 may decompose subsignal 42A (FIG. 3A) into a plurality of subsignals by repeating subsignal 48A, as shown by subsequent subsignals 48B, 48C, until a stimulation envelope similar to envelope 45A defined by the original stimulation signal 42A is achieved.

In the example shown in FIG. 3C, subsignal 49A represents a subsignal similar to subsignal 48A that has been cut short at time $T_1$, thereby defining a subsignal 49A with a shorter pulse width. Subsignal 48A is repeated until reaching time $T_1$, which indicates the end of the original stimulation signal 42A. Parameter generator 38 may then determine the pulse width (denoted as $T_6$) of subsignal 49A that remains at the end of the pulse train 51. In the example shown in FIG. 3C, pulse width $T_6$ of subsignal 49A is generally equal to the difference between pulse width $T_1$ of signal 42A (or the signal envelope 45A) and the sum of the pulse widths of each subsignal 48A-48C and the time interval 50 between subsignals 48. In this way, parameter generator 38 decomposes stimulation signal 42A into a plurality of subsignals 48A-48C, 49A and generates a pulse train 51 that may be substituted for stimulation signal 42A. As previously indicated, it may be desirable to maintain stimulation envelope 45A of signal 42A in order to help maintain the therapeutic effects of stimulation therapy based on the therapy program defining stimulation signal 42. Subsignals 48D-48F, 49B may be generated in substantially similar manner as subsignals 48A-48C, 49A, respectively. Subsignals 48D-48F, 49B may be generated based on signal 42B (FIG. 3A) and the respective signal envelope 45B.

In the example shown in FIG. 3C subsignals 48A-48C and 48D-48F are shown to have substantially similar pulse widths. In other examples, each of subsignals 48A-48C generated based on subsignal 42A, and each one of subsignals 48D-48F generated based on subsignal 42B may have different pulse widths. For example, processor 24 may set the pulse width of subsignal 48A such that the energy associated with subsignal 48A is equal to the threshold energy value 36 of IMD 14. Processor 24 may then set the pulse width of subsignal 48B to be less than the pulse width of subsignal 48A such that the energy associated with subsignal 48B is less than the threshold value. Other variations between subsignal 48, 49 durations (i.e., pulse widths in the case of stimulation pulses) are contemplated.

As shown in FIG. 3C, subsignal 49A is shown at the end of the pulse train 51. However, processor 24 may generate therapy parameters such that subsignal 49A occurs earlier in pulse train 51 rather than at the end of pulse train 51. For example, processor 24 may program subsignal 49A to occur between subsignal 48A and subsignal 48B.

Processor 24 of IMD 14 may select the time interval 50 between subsignals 48, 49. In one example, processor 24 may set time interval 50 such that each time interval 50 less than the duration of the carry-over effect from delivery of stimulation signal 48, respectively. This minimizes the possibility that patient may feel any adverse consequences of therapy delivery to patient 12 according to the plurality of subsignals 48, 49 compared to the delivery of original stimulation signals 42 defined by a therapy program. In particular, if each time interval 50 is less than the duration of the carry-over effect generated by delivery of each subsignal 48, respectively, patient 12 may not feel any interruptions between the delivery of stimulation subsignals 48, 49, and the physiological effects from therapy delivery by subsignals 48, 49 may be substantially similar to therapy delivery by signal 42. In other examples, however, processor 24 may set each time interval 50 to be greater than the duration of the carry-over effect.

Based on the pulse width $T_5$ of subsignals 48 and the time interval 50 between subsignals 48, 49, parameter generator 38 may determine a pulse rate for the subsignals 48, 49. For example, parameter generator 38 may determine a period for each subsignal 48, which substantially equals the sum of the pulse width $T_5$ and a time interval 50. The pulse rate may then be determined as the inverse of the period.

Processor 24 may control stimulation generator 30 (FIG. 2) to deliver stimulation to patient 12 according to the modified therapy program. In particular, under the control of processor 24, stimulation generator 30 may deliver stimulation according to the plurality of subsignals 48, 49. For example, stimulation generator 30 may generate and deliver stimulation based on the pulse train comprising subsignals 48, 49, where the rate at which the pulse train is repeated is based on the frequency of the original therapy program. In the example shown in FIG. 3C, the interval 56 between stimulation signals 42 is maintained between the pulse trains defined by 48, 49.

In some examples, parameter generator 38 may transmit the modified therapy program to stimulation generator 30. The modified therapy program may define pulse width $T_5$ of each subsignal 48, pulse width $T_6$ of subsignal 49. In addition, the modified therapy program may define at least one of the pulse rate of subsignal 48A-48C, 49A within pulse train 51 (or the pulse rate of subsignals 48D-48F, 49B associated with original stimulation signal 42B or the time interval 50 between subsignals 48A-48C, 49A and between signals 48D-48F, 49B. The pulse rate (or frequency) of subsignals 48A-48C, 49A may be defined by the inverse of the sum of the pulse width $T_5$ and the time interval 50 between subsignals 48A-48C, 49A. The pulse rate of subsignals 48D-48F, 49B may be substantially similar to the pulse rate of subsignal 48A-48C, 49A.

In other examples, parameter generator 38 may transmit all the therapy parameter values for the modified therapy program, rather than only the parameter values that were actually modified. If desired, the modified therapy parameters may be stored within memory 26 as a therapy program 37, or with unmodified therapy parameters of the original program as a modified program 37. Processor 24 may control stimulation generator 30 to generate and deliver therapy according to a modified therapy program.

FIG. 3D illustrates a schematic timing diagram illustrating another example of a technique for decomposing each of the stimulation signals 42 (FIG. 3A) into a plurality of subsignals 53A-53H (collectively referred to as "subsignals 53"), with the aid of a timing window 52. As shown in FIG. 3D, timing window 52 defines a timing window for subsignal 53A. The timing windows for subsignals 53B-53H may be substantially similar to timing window 52. As described in further detail below, timing window 52 defines the period and pulse rate for each of the subsignals 53A-53H.

In the example shown in FIG. 3D, the plurality of subsignals 53A-53D associated with original stimulation signal 42A define a pulse train 54A. Pulse train 54B is defined by subsignals 53E-53H in a manner substantially similar to that of pulse train 54A. Each pulse train 54 may be separated by the original time interval 56 between stimulation signals 42, e.g., based on the frequency and pulse width of stimulation signals 42 defined by the original therapy program.

Subsignals 53A-53D are repeated within pulse train 54A until the pulse train 54A substantially mimics stimulation envelope 45A defined by the original stimulation signal 42A. Similarly, subsignals 53E-53H are repeated within pulse train 54B to substantially mimic stimulation envelope 45B defined by the original stimulation signal 42B. Subsignals 53 within each pulse train 54A, 54B are spaced from a subsequent subsignal 53 by time interval 55. In some examples, parameter generator 38 may be programmed with values defining timing window 52. Timing window 52 may have an arbitrary duration that is less than the duration (e.g., the pulse width) of stimulation signal 42. The pulse width of each of the subsignals 53 may be selected such that the energy associated with each of the subsignals 53 is less than or equal to the threshold value 36 of IMD 14. In some examples, the total energy of subsignals 53 may be less than or equal to the energy associated with stimulation signal 42A, while in other examples, total energy of subsignals 53 may be greater than or equal to the energy associated with stimulation signal 42A. In some examples, interval 55 is less than the duration of a carry-over effect that results from delivery of one of the stimulation signals 53.

In one example, parameter generator 38 sets the duration of timing window 52 based on a ratio between the duration of the original stimulation signal 42A defined by the therapy program and the desired maximum duration of each subsignal 53. For example, if stimulation signal 42A defined by the therapy program comprises a period of approximately 10 milliseconds (ms) (i.e., an approximately 100 Hz signal), timing window 52 may have a duration of approximately 0.01 ms, which represents a 1/1000 ratio. The numerical values of the stimulation pulse, timing window interval, and ratio are merely examples. Different examples may use different parameters with different values than the example provided. Timing window 52 may not be less than the inverse of the maximum pulse rate that IMD 14 can generate.

In general, parameter generator 38 may select the duration of each subsignal 53 and/or the duration of the time interval 55 between subsequent subsignals 53 in order to determine the parameter values of subsignals 53. For example, using the decomposition of original stimulation signal 42A as an example, in one example, parameter generator 38 may substantially maintain amplitude $A_1$ of stimulation signals 42 for subsignals 53A-53D, and modify the pulse width of each of the subsignals 53A-53D with the aid of timing window 52.

Timing window 52 may provide a time frame for determining the pulse width of each subsignal 53 and the time interval 55 between subsignals 53. Parameter generator 38 may select the pulse width of each subsignal 53 and determine the time interval 55 between subsequent subsignals 53 based on timing window 52. For example, parameter generator 38 may determine the pulse width for subsignal 53A at which the energy of subsignal 53A with an amplitude A1 is less than or equal to the energy threshold value 36 (FIG. 2). Parameter generator 38 may then determine time intervals 55 between subsignals 53A-53D to be the difference between the duration of timing window 52 and the selected pulse width of subsignal 53.

As another example, parameter generator 38 may select the time interval 55 between subsequent subsignals 53A-53D prior to determining the pulse width of subsignals 53A-53D For example, parameter generator 38 may select the time interval 55 such that the pulse rate of subsignals 53A-53D in pulse train 54A does not exceed the switching capability of IMD 14. Parameter generator 38 may then determine the pulse width of each subsignal 53, e.g., to be substantially equal to the difference between the duration of timing window 52 and the selected time interval 55.

As another example, parameter generator 38 may select the parameters for pulse train 54A such that the pulse width of each subsignal 53A-53D in pulse train 54A and the time interval 55 between subsignals 53A-53D results in a time interval 55 that does not exceed (e.g., is not greater than or equal to) the carryover effect from delivery of one of the stimulation subsignals 53A-53D. The duration of subsignal 53A may affect the duration of the carryover effect, hence, the duration of subsignal 53A may affect the duration of time interval 55. However, the duration of subsignal 53A and time interval 55 may be substantially equal to timing window 52.

Parameter generator 38 may select the parameters (e.g., pulse width, pulse rate, and/or time intervals 55) for subsignals 53E-53H of pulse train 54B using techniques substantially similar to those described with respect to subsignals 53A-53D of pulse train 54A.

After determining a pulse width for subsignals 53, energy calculator 34 (FIG. 2) of IMD 14 may determine an energy associated with each subsignal 53 using the techniques for determining an energy associated with a stimulation signal. Processor 24 may compare the energy associated with each subsignal 53 to energy threshold value 36. If the energy associated with each subsignal 53 is less than the energy threshold value 36, parameter generator 38 may transmit the modified therapy parameters to processor 24, memory 26 or directly control stimulation generator 30 to generate and deliver therapy based on the modified therapy parameters. The modified parameters may include the pulse width of each subsignal 53, as well as the frequency of the subsignals 53 within the pulse train 54 (i.e., the time interval 55 between subsignals 53).

The frequency of subsignals 53 within each pulse train 54 may be determined based on the timing window 52. For example, clock source 40 (FIG. 2) of IMD 14 may output a clock signal that defines a period that is substantially equal to the duration of timing window 52. Parameter generator 38 may then generate instructions that cause stimulation generator 30 to transmit subsignal 53 every period of clock source 40. The pulse rate of subsignals 53 within each pulse train 54 may be the inverse of the duration of timing window 52 because the size of the timing window effectively defines a period of subsignals 53. Parameter generator 38 may generate a subprogram comprising the pulse width of subsignals 53 and time interval 55.

In another example, if the energy associated with subsignal 53 defined by the timing window is greater than the threshold value 36, parameter generator 38 may reduce the duration of timing window 52. For example, decreasing the duration of time window 52 may effectively decrease the time interval 55 between stimulation subpulses 53, effectively decrease the pulse width of each stimulation pulse 53 or a combination of decreasing the time interval 55 and pulse width of subpulses 53. After modifying timing window 52, energy calculator 34 may redetermine the energy of each subsignal 53, and processor 24 may compare the determined value to energy threshold value 36. If the energy associated with the subsignal is still greater than the energy threshold value 36, the process of reducing the size of the timing window may repeat until the energy associated with an electrical pulse defined by the timing window is less than the energy threshold value.

In another example, if the energy associated with subsignal 53 is greater than the maximum energy threshold value, parameter generator 38 may maintain the same duration of timing window 52 and increase the time interval 55 between subsignals 53 or decrease the pulse width of subsignals 53.

In each of the examples described above with respect to FIGS. 3A-3D, the modified therapy programs may be stored within IMD 14 and/or programmer 20. The modified therapy programs may be referred to as subprograms. A clinician may later analyze the modifications made to the therapy programs in order to determine whether any hardware changes to therapy system 10 or other changes to the therapy programs are desirable.

Figure 4:
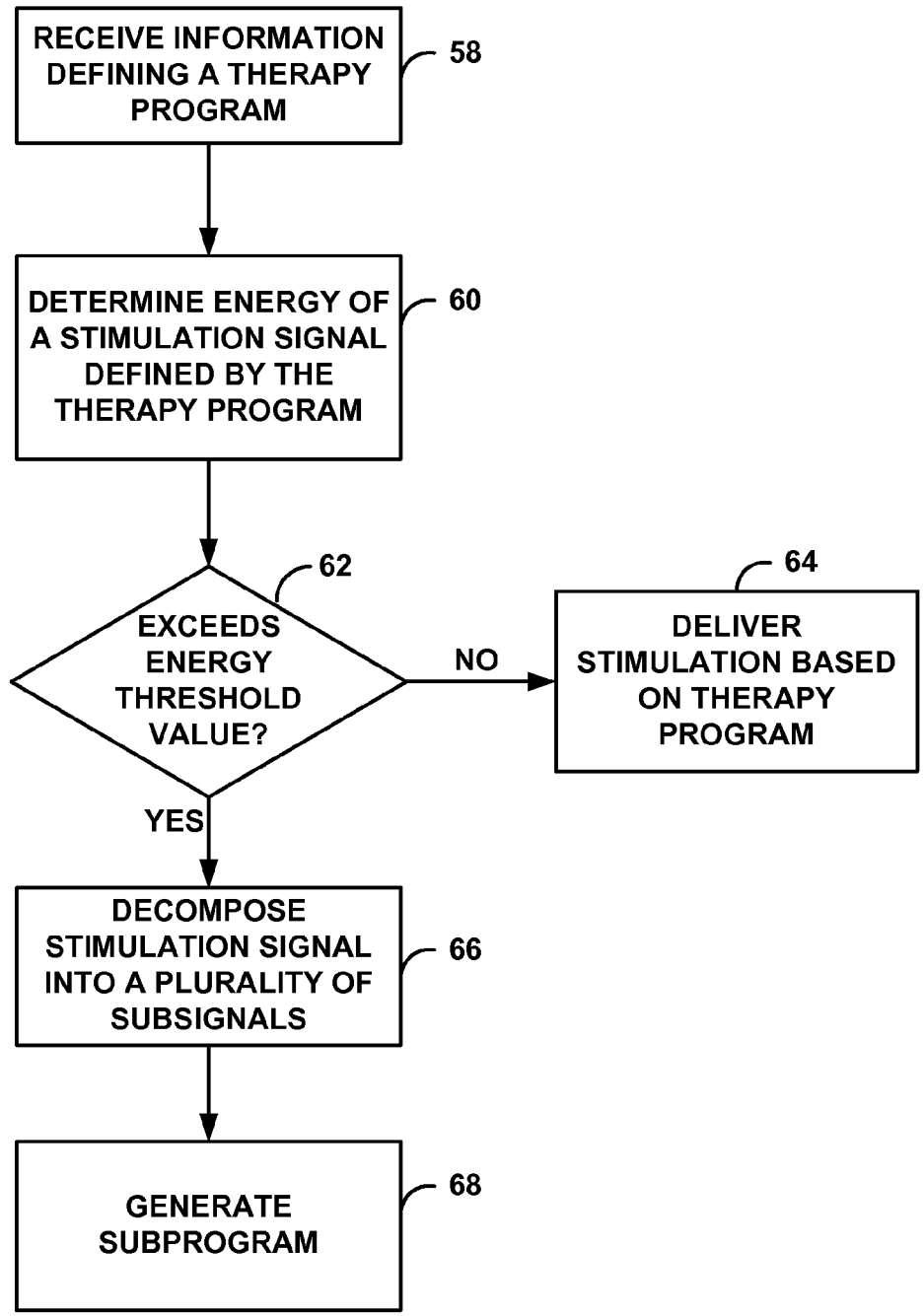
FIG. 4 is a flow diagram illustrating an example technique for decomposing a stimulation signal into a plurality of subsignals.

FIG. 4 is a flow diagram illustrating an example technique that IMD 14 may implement in order to determine whether to decompose an electrical stimulation signal defined by a therapy program into a plurality of subsignals. While IMD 14 is primarily referred to in the description of FIG. 4, in other examples, programmer 20 or another computing device may perform any part of the technique shown in FIG. 4 in order to determine whether to modify a therapy program to decompose a stimulation signal into a plurality of subsignals that are each associated with a lower energy than the stimulation signal.

Processor 24 of IMD 14 may receive information that defines a therapy program (58). For example, processor 24 may receive a signal from programmer 20 or another device via telemetry interface 28, or processor 24 may select a therapy program from memory 26 (FIG. 2). Energy calculator 34 determines the energy associated with the received stimulation signal (60). Energy calculator 34 may determine the energy associated with the received stimulation signal by, for example, multiplying the duration of the electrical stimulation signal defined by the therapy program with the amplitude of the electrical stimulation signal.

Processor 24 may compare the DETERMINED energy of the stimulation signal with the energy threshold value 36 stored in memory 26 (62). In one example, energy threshold value 36 is the value of the maximum energy of a stimulation signal that IMD 14 may generate. If the determine energy is less than the energy threshold value 36 (NO of 62), processor 24 may control stimulation generator 30 to generate and deliver therapy to patient 12 based on the therapy program defining the stimulation signal (64). On the other hand, if the determined energy is greater than or equal to the energy threshold value 36, or, in some cases, greater than or equal to the energy threshold value 36 (YES of 62), parameter generator 38 may modify the therapy program to decompose the stimulation signal defined by the therapy program into a plurality of subsignals that each have an energy that is less than or equal to the energy threshold value 36 (66).

In one example, parameter generator 38 generates the parameter values for the plurality of subsignals by determining an acceptable pulse width of a subsignal having substantially the same amplitude as the stimulation signal defined by the therapy program. The acceptable pulse width may be the pulse width at which a single subsignal has an energy that is less than or equal to the energy threshold value. Parameter generator 38 may also determine the intervals of time between each subsignal. For example, parameter generator 38 may generate an interval of time such that each subsignal is spatially separated by an interval of time that is less than the duration of a carry-over effect of the stimulation signal.

Stimulation generator 30 may generate a subprogram comprising therapy parameters based on the modified therapy program (68). For example, parameter generator 38 may provide the pulse width and pulse rate of the subsignal to processor 24 for control of stimulation generator 30, where the pulse rate is defined by the pulse width and the spacing between subsignals. Parameter generator 38 or processor 24 may determine the spacing between subsignals based on the provided pulse rate. In some examples, the modified therapy program may be stored in memory 26.

Figure 5:
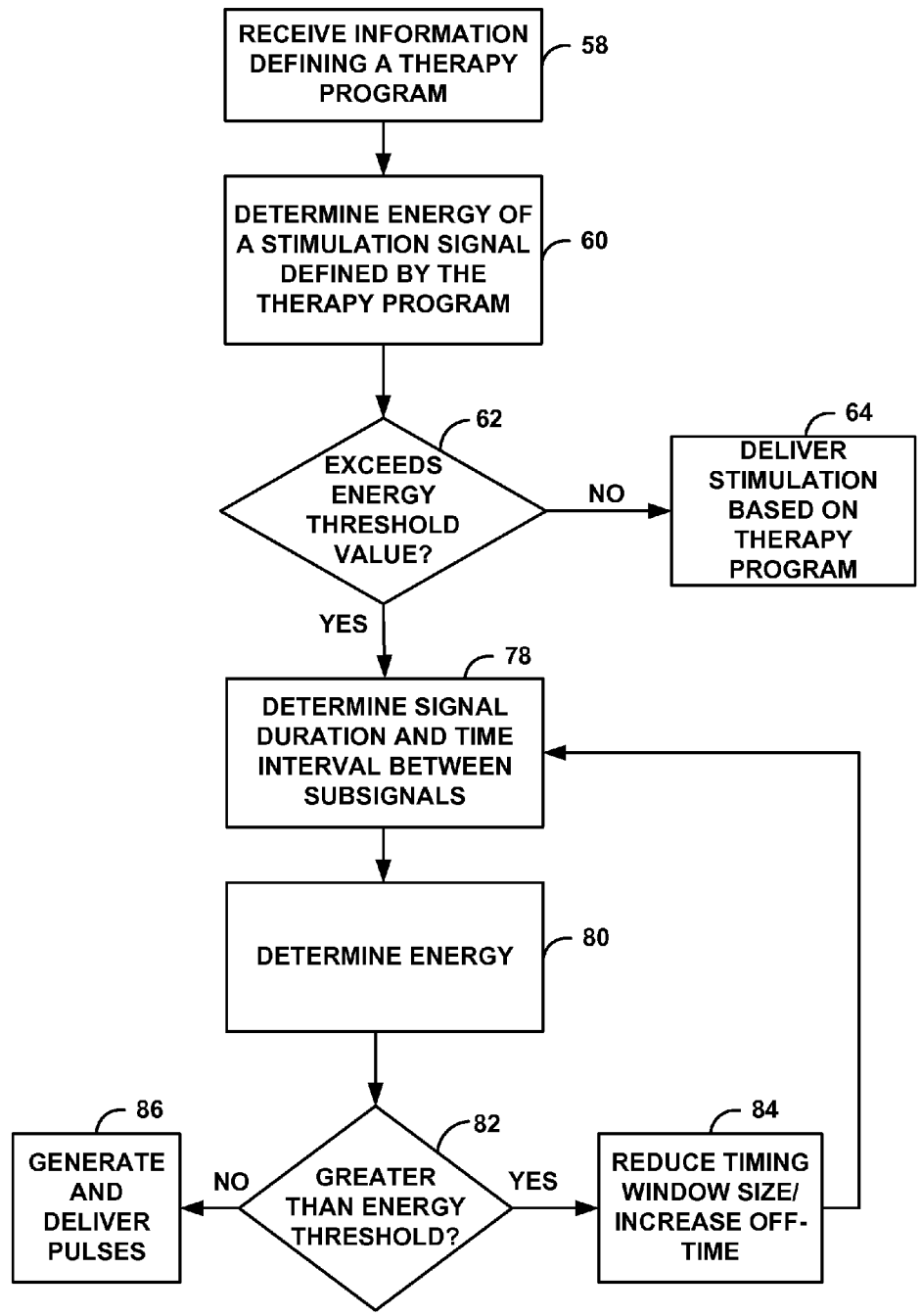
FIG. 5 is a flow diagram illustrating another example technique for decomposing a stimulation signal into a plurality of subsignals.

FIG. 5 is a flow diagram illustrating another example technique that parameter generator 38 may implement in order to decompose an electrical stimulation signal defined by a therapy program into a plurality of subsignals. Processor 24 of IMD 14 may receive information that defines a therapy program (58). Energy calculator 34 determines the energy associated with the stimulation signal defined by the therapy program (60). Processor 24 compares the determined energy of the stimulation signal with the energy threshold value 36 stored in memory 26 (62) in order to determine whether to decompose the stimulation signal defined by the therapy program into a plurality of subsignals that each have a lower energy than the stimulation signal. In some examples, the energy threshold value is the value of the maximum energy that IMD 14 may produce.

If the determined energy is less than the energy threshold value 36 (NO of 62), processor 24 may control stimulation generator 30 to generate and deliver therapy to patient 12 based on the therapy program defining the stimulation signal (64).

On the other hand, if the determined energy is greater than, and, sometimes, equal to, the threshold energy value 36 (YES of 62), parameter generator 38 decomposes the stimulation signals and generates therapy parameter values to define a plurality of subsignals that each have an energy lower than the energy of the stimulation signal. In the example technique shown in FIG. 5, parameter generator 38 determines the time interval 55 between subsignals 53 (FIG. 3D) and the duration of the subsignals 53 with the aid of timing window 52 (78). For example, parameter generator 38 may select each time interval 55 to be less than or equal to the duration of a carry-over effect of the stimulation signal. Parameter generator 38 may also set the pulse width of each subsignal 53, where the pulse width is the difference between the size of timing window 52 and a single time interval 55. After setting the pulse width and time interval 52 for a given timing window 52, energy calculator 34 may determine the energy of the resulting subsignal 53 (80).

Processor 24 may compare the energy of one or more subsignals 53 and the energy threshold value 36 (82). If the determined energy for the subsignal 53 is greater than energy threshold value 36 (YES of 82), parameter generator 38 may maintain the selected time interval 55 between subsignals 53 and decrease the duration of the timing window 52, thereby decreasing the pulse width and substantially maintaining the same time interval 55 (84). In another example, parameter generator 38 may maintain the duration of timing window 52, and increase time interval 55 between pulses 53, thereby decreasing the pulse width (84). In yet another example, parameter generator 38 may increase the duration of timing window 52 (84). In such examples, the pulse width of subsignals 53 may be increased to the duration of timing window 52, and the amplitude of subsignals 53 may be decreased. However, in some cases, it may be undesirable to define a time interval 55 that is greater than the duration of a carry-over effect from delivery of the electrical stimulation subsignal.

After reducing the pulse width of subsignal 53, energy calculator 34 may redetermine the energy associated with subsignal 53, and processor 24 may compare the energy to the threshold energy value 36. The process of decreasing the pulse width of subsignal 53 may be repeated until the energy associated with the subsignal 53 is less than energy threshold value 36. Processor 24 may control stimulation generator 30 to generate and deliver stimulation signals according to a subprogram comprising therapy parameters based on the modified therapy program (86).

Parameter generator 38 may determine the frequency of subsignals 53 within each pulse train 54 associated with the original stimulation signal 42. In one example, the frequency of subsignals 53 within each pulse train 54 is determined based on the duration of timing window 52. For example, parameter generator 38 may cause clock source 40 to generate a clock signal whose period is substantially equal to the duration of the timing window 52. Parameter generator 38 may provide the pulse width and off-time to stimulation generator 30 at every period of the clock signal generated by clock source 40.

Figure 6:
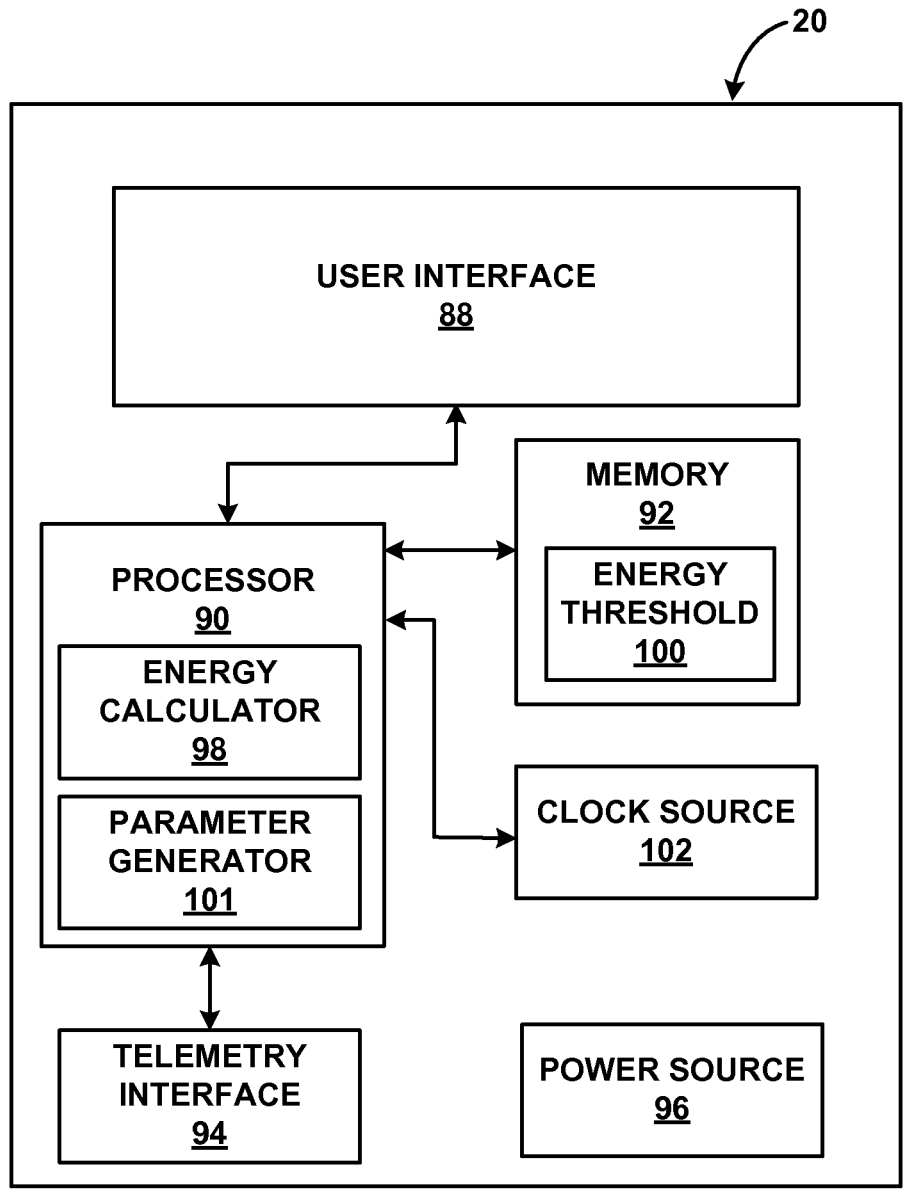
FIG. 6 is a functional block diagram illustrating various components of an example programmer.

FIG. 6 is a functional block diagram illustrating various components of an external programmer 20. The techniques for decomposing a stimulation signal defined by a therapy program into a plurality of subsignals described above with respect to the various components of IMD 14 may be performed by external programmer 20 or another external computing device. External programmer 20 may generate a modified therapy program that defines a plurality of subsignals based on a stimulation signal defined by a therapy program, and may provide the modified therapy program to IMD 14. IMD 14 may deliver therapy to patient 12 in accordance with the modified therapy program.

As shown in FIG. 6, external programmer 20 includes user interface 88, processor 90, memory 92, telemetry interface 94, power source 96, and clock source 102. Processor 90 includes energy calculator 98 and parameter generator 101. Although processor 90 includes energy calculator 98 and parameter generator 101 in the example shown in FIG. 6, in other examples, energy calculator 98 and parameter generator 101 may be embodied in one or more separate processors.

Memory may include any volatile, non-volatile, magnetic, optical, or electrical media, such as RAM, ROM, NVRAM, EEPROM, flash memory, any other digital media, or any combination thereof. Memory 26 may store instructions for execution by processor 90, stimulation therapy program data, sensor data (if applicable), operational and status data of IMD 14 and patient 12, and any other information regarding therapy or patient 12.

Memory also stores energy threshold value 100, which may be similar to energy threshold value 36 stored in memory 26 of IMD 14 (FIG. 2). In the case of a clinician programmer, a clinician may interact with user interface 88 in order to generate therapy programs for therapy system 10 and/or adjust parameter values of the therapy programs, such as voltage or current amplitude values, pulse width values, pulse rate values, electrode combinations and electrode polarities. Generation of therapy programs and adjustment of program parameters may be aided by automated programming algorithms that guide the physician or clinician to select particular programs and program parameters. In the case of a patient programmer, a patient may interact with user interface 88 to select programs and adjust program parameters, e.g., on a limited basis as specified by the physician or clinician.

User interface 88 may include a display and one or more input buttons (not shown) that allow external programmer 20 to receive input from a user. The display may be a liquid crystal display (LCD), a light emitting diode display, a dot matrix display, touch screen or any other suitable display for presenting information to a user. The input buttons may include a touch pad, increase and decrease buttons, emergency shut off button, and other buttons needed to control the stimulation therapy. In some cases, the user may interact with user interface 88 via a stylus, soft keys, hard keys, directional devices, and any of a variety of other input media. Memory 92 may include operational instructions for processor 90 or program parameter sets.

Processor 90 may include one or more microprocessors, DSPs, ASICs, FPGAs, or any other equivalent integrated or discrete logic circuitry. Functions attributed to processor 90 herein may be embodied as hardware, firmware, software, or any combination thereof. Processor 90 receives input from user interface 88, presents data via the user interface, retrieves data from memory 92 and stores data within the memory. Processor 90 also controls the transmission of data to IMD 14 with the aid of telemetry interface 94. Telemetry interface 94 may communicate automatically with telemetry interface 28 of IMD 14 (FIG. 2) at a scheduled time or when telemetry interface 94 detects the proximity of IMD 14. Alternatively, telemetry interface 94 may communicate with IMD 14 at the prompt of a user, e.g., upon receipt of user input through user interface 88. To support RF communication, telemetry interface 94 may include appropriate electronic components, such as amplifiers, filters, mixers, encoders, decoders, modulators, demodulators and the like.

Power source 96 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In examples in which external programmer 20 modifies a therapy program based on information indicating the therapy program defines a stimulation signal that exceeds an energy threshold value 100, energy calculator 98 may perform the same functions as energy calculator 34 (FIG. 2) of IMD 14. Processor 90 may perform the same functions as processor 24 (FIG. 2) of IMD 14. Parameter generator 101 may perform the same functions as parameter generator 38 (FIG. 2) of IMD 14. Clock source 102 may perform the same functions as clock source 40 (FIG. 2) of IMD 14. Furthermore, in some examples, energy calculator 98, parameter generator 101, and clock source 102 may be a part of processor 90, e.g., may be functions performed by processor 90 with the aid of firmware, hardware, software or any combinations thereof.

As described above, therapy system 10 may be used to deliver electrical stimulation to one or more target tissue sites within patient 12, where the target tissue site may include tissue proximate to a nerve, nerve branch, smooth muscle fiber or skeletal muscle fiber. The target tissue site may encompass a relatively large area. In some cases, a therapy program that that defines an electrical stimulation signal that delivers efficacious therapy to the target tissue site may exceed the energy threshold value 36 of IMD 14 (or energy threshold value 100 stored by programmer 20). Instead of or in addition to decomposing the stimulation signal into a plurality of subsignals, IMD 14 may divide the target tissue site into a plurality of subregions, and provide stimulation to each one of the subregions while substantially maintaining the therapeutic effects of the therapy.

Figure 7:
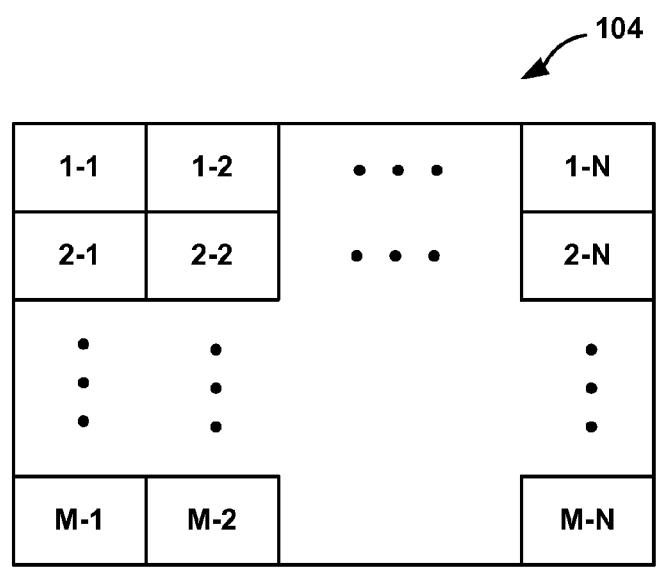
FIG. 7 is a conceptual diagram illustrating an example surface area of a target tissue.

FIG. 7 is a schematic illustration of target tissue site 104. For ease of illustration and description, tissue site 104 is illustrated as a two-dimensional rectangular shape. However, target tissue site 104 may be any regular or irregular two-dimensional cross-sectional shape or three-dimensional volume. Target tissue site 104 may be divided into a plurality of subregions. The subregions are shown in FIG. 7 as 1-1 to M-N. Although the subregions are each rectangular as shown in FIG. 7, in other examples, the subregions of target tissue site 104 may be any suitable shape and size, and the different subregions may have different shapes and sizes.

Rather than delivering stimulation that generates a stimulation field that covers the entire target tissue site 104, IMD 14 may deliver stimulation to subsets of the subregions of tissue site 104 at different times. Subdividing target tissue site 104 into subregions may help decrease the energy of each of the stimulation signals delivered by IMD 14. For example, an energy required to activate or otherwise provide therapy to one of the subregions or a subset of the subregions of target tissue site 104 may be less than energy required to stimulate the entire target tissue site 104 via a stimulation signal. The energy required to activate or otherwise provide therapy to one of the subregions or a subset of the subregions may be less than the energy threshold of IMD 14. Each subregion will activate different tissue, and, accordingly, maintaining the stimulation rate of the therapy program and the coverage of the therapy will provide effective therapy in many cases, despite the sequential nature of the stimulation.

A stimulation field covering less than the entire tissue site 104 may be generated by selecting different combinations of electrodes 17A, 17B of leads 16A, 16B (FIG. 2), respectively, and/or by selecting different stimulation parameter values. IMD 14 may deliver electrical stimulation signals (e.g., to stimulate) each one of the plurality of surfaces or volumes in a sequential fashion and within a range of time that enables patient 12 to receive the cumulative effect of the stimulation, while not perceiving the transition from the stimulation of one subregion to another. For example, IMD 14 may deliver electrical stimulation to subregion 1-1, then 1-2, until reaching M-N. In other examples, IMD 14 may deliver electrical stimulation two or more subregions substantially simultaneously, where the energy required to stimulate more than one of the plurality of subregions is less than the maximum energy threshold value of IMD 14. Other techniques for deliver stimulation to the subregions of target tissue site 104 are contemplated.

In the techniques described above, a stimulation signal defined by a therapy program is decomposed into a plurality of subsignals based on an energy threshold value, e.g., in order to increase an energy efficiency of IMD 14 or due to energy limitations of IMD 14. In addition to or instead of decomposing the stimulation signal into a plurality of subsignals, a therapy field that is generated by therapy delivery by IMD 14 according to a therapy program may be decomposed into a plurality of therapy subfields based on a comparison between an energy associated with the therapy program and an energy threshold value. For example, as described in further detail below, with the aid of a computing device, an algorithmic model of a therapy field may be generated based on a therapy program in order to aid the decomposition of the field into a plurality of therapy subfields.

Figure 8:
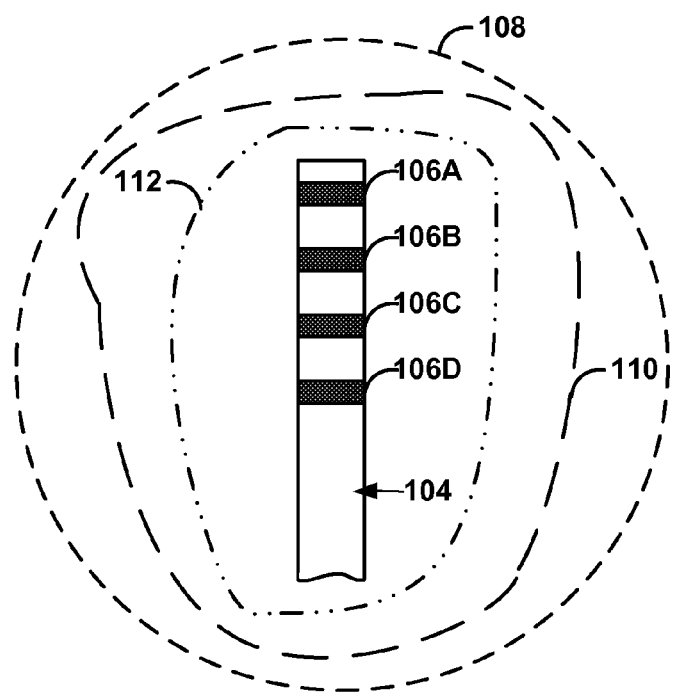
FIG. 8 is a schematic illustration of different types of therapy fields.

FIG. 8 is a conceptual illustration of different types of therapy fields that may be generated when IMD 14 delivers electrical stimulation signals to patient 12 via electrodes 106A-106D of lead 104. For ease of illustration, two-dimensional cross-sectional profiles of three-dimensional fields are illustrated herein. Lead 104 may be coupled to IMD 14 instead of or in addition to leads 16. As shown in FIG. 8, lead 104 includes four electrodes 106A-106D (collectively referred to as "electrodes 106"). Electrodes 106 may be similar to electrodes 17 of leads 16 (FIG. 1). The type and number of electrodes shown in FIG. 8 are merely one example. In other examples, lead 104 may comprise any suitable number of electrodes. In addition, in some examples, electrodes 106 may be segmented or partial ring electrodes that define a complex electrode array.

In some examples, the therapy field that is decomposed into a plurality of therapy subfields may include a stimulation field 108, an electrical field 110 or an activation field 112. Stimulation field 108 defines the field generated when IMD 14 delivers electrical stimulation signals according to a therapy program via electrodes 106. Although stimulation field 108 is depicted in two dimensions in FIG. 8, stimulation field 108 is three dimensional and covers a volume of patient tissue. The size (e.g., volume) and shape of stimulation field 108 may differ based on the stimulation parameter values of a therapy program, such as the stimulation signal voltage or current amplitude and the activated electrodes 106, as well as the polarities of the selected subset of electrodes 106.

Electrical field 110 represents the areas of a patient anatomical region that will be covered by an electrical field during therapy when stimulation field 108 is generated within patient 12. Although electrical field 110 is shown in two dimensions in FIG. 8, electrical field 110 is three-dimensional. Electrical field 110 may define the volume of tissue that is affected when electrodes 106 are activated. The size and shape of electrical field 110 may be different in different examples, and may depend upon the characteristics of the patient's tissue proximate to electrodes 106. Relevant tissue characteristics include tissue conductivity or density.

Activation field 112 represents the neurons that will be activated by electrical field 110 in the neural tissue proximate to electrodes 106. Accordingly, activation field 112 may be based on the therapy parameter values of the therapy program, electrical field 110, and the characteristics of tissue encompassed by stimulation field 108, such as the tissue conductivity or density. Although activation field 112 is shown in two dimensions in FIG. 8, activation field 112 is three-dimensional.

In some examples, processor 90 of programmer 20 (FIG. 6) or another computing device may generate an algorithmic model a therapy field, such as stimulation field 108, electrical field 110, and/or activation field 112, to aid in the modification of a therapy program if the energy associated with the therapy program exceeds an energy threshold value. While programmer 20 and its functional components are primarily referred to in the description of FIGS. 8-16, in other examples, IMD 14 or another device may perform any part of the techniques described herein. The algorithm for generating an algorithmic model of a stimulation field may be stored in memory 26 (FIG. 2) of IMD 14, memory 92 (FIG. 6) of external programmer 20 or a memory of another device. An algorithmic model of a therapy field may be generated with the aid of modeling software, hardware or firmware executing on a computing device, such as programmer 20 or a separate dedicated or multifunction computing device.

Example algorithms for generating algorithmic models of stimulation fields, electrical fields, and activation fields are described in commonly-assigned U.S. Pat. No. 7,822,483 issued on Oct. 26, 2010 to Stone et al., entitled, "ELECTRICAL AND ACTIVATION FIELD MODELS FOR CONFIGURING STIMULATION THERAPY" and filed on Oct. 31, 2006, and commonly-assigned U.S. Pat. No. 8,380,321 issued on Feb. 19, 2013 to Goetz et al., entitled, "PROGRAMMING INTERFACE WITH A CROSS-SECTIONAL VIEW OF A STIMULATION LEAD WITH COMPLEX ELECTRODE ARRAY GEOMETRY," and filed on Oct. 31, 2006. The entire content of U.S. Pat. Nos. 7,822,483 and 8,380,321 are incorporated herein by reference.

In one example, processor 90 of programmer 20 generates an algorithmic model of an electrical field model based upon patient anatomy data and a therapy program defining stimulation parameter values, where the electrical field model represents the areas of a patient anatomical region that will be covered by an electrical field during therapy. The patient anatomy data may include at least one of an anatomical image of a patient, a reference anatomical image, an anatomical atlas or a tissue conductivity data set. The patient anatomy data may be specific to patient 12 or may represent data for more than one patient, e.g., model or averaged data of the anatomical structure and tissue conductivity of multiple patients. For example, in some examples, the patient anatomy data may include tissue conductivity data or other relevant tissue data that is typical for the particular lead location for the particular therapeutic application (e.g., SCS in the case of therapy system 10 of FIG. 1), and may be, but need not be, specific to patient 12. Patient anatomy data may indicate one or more characteristics of patient tissue proximate to an implanted lead, and may be created from any type of imaging modality, such as, but not limited to, computed tomography (CT), magnetic resonance imaging (MRI), x-ray, fluoroscopy, and the like.

The algorithmic model of the electrical field may estimate tissue that will be affected by the stimulation field. Due to the conductivity or impedances of tissue proximate electrodes 106 (FIG. 8) of lead 104, a stimulation field may affect only some parts of the tissue proximate the implanted electrodes. The electrical field may be estimated by modeling the tissue around electrodes 106 and determining the propagation of the electrical field from electrodes 106 based on the characteristics (e.g., impedance) of the tissue proximate to electrodes 106.

In another example, processor 90 of programmer 20 may generate an algorithmic model of an activation field that is based on a neuron model that indicates one or more characteristics of patient neural tissue proximate to implanted lead 104. The activation field indicates the neurons that will be activated by the electrical field in the anatomical region. In general, an electrical field may be indicative of the electrical propagation through the tissue surrounding lead 104, while an activation field may be indicative of the neurons that are actually activated by the electrical field.

Different techniques may be employed to generate an algorithmic model a therapy field that is generated upon therapy delivery by a medical device according to a therapy program. In some examples, programmer 20 includes a user interface that enables a clinician to program IMD 14 by defining one or more stimulation fields and processor 90 may subsequently generate the therapy programs that may achieve the defined stimulation fields, as described in commonly-assigned U.S. Pat. No. 7,822,483 issued on Oct. 26, 2010 to Stone et al. and U.S. Pat. No. 8,380,321 issued on Feb. 19, 2013 to Goetz et al. The therapy field may be based on the stimulation field defined by the clinician, and may be, for example, the stimulation therapy field, an electrical field based on the stimulation field or an activation field.

The techniques described in U.S. Pat. No. 7,822,483 to Stone et al. and U.S. Pat. No. 8,380,321 to Goetz et al. may also be used to generate an algorithmic model of a therapy field after a therapy program is generated. For example, after programming IMD 14 with a therapy program that provides efficacious therapy to patient 12, a user may generate an electrical field model that estimates where the electrical current will propagate from the electrodes 106 of implanted leads 104 (or electrodes of any other implanted lead) or an activation field model that estimates which neurons within the electrical field model will be activated by the voltage of the electrical field during therapy. In general, the electrical field model or the activation field model may estimate the anatomical structures that will be affected by a therapy program. Thus, the electrical field model or the activation field model may represent a therapy field that is generated based on a therapy program.

Figure 9:
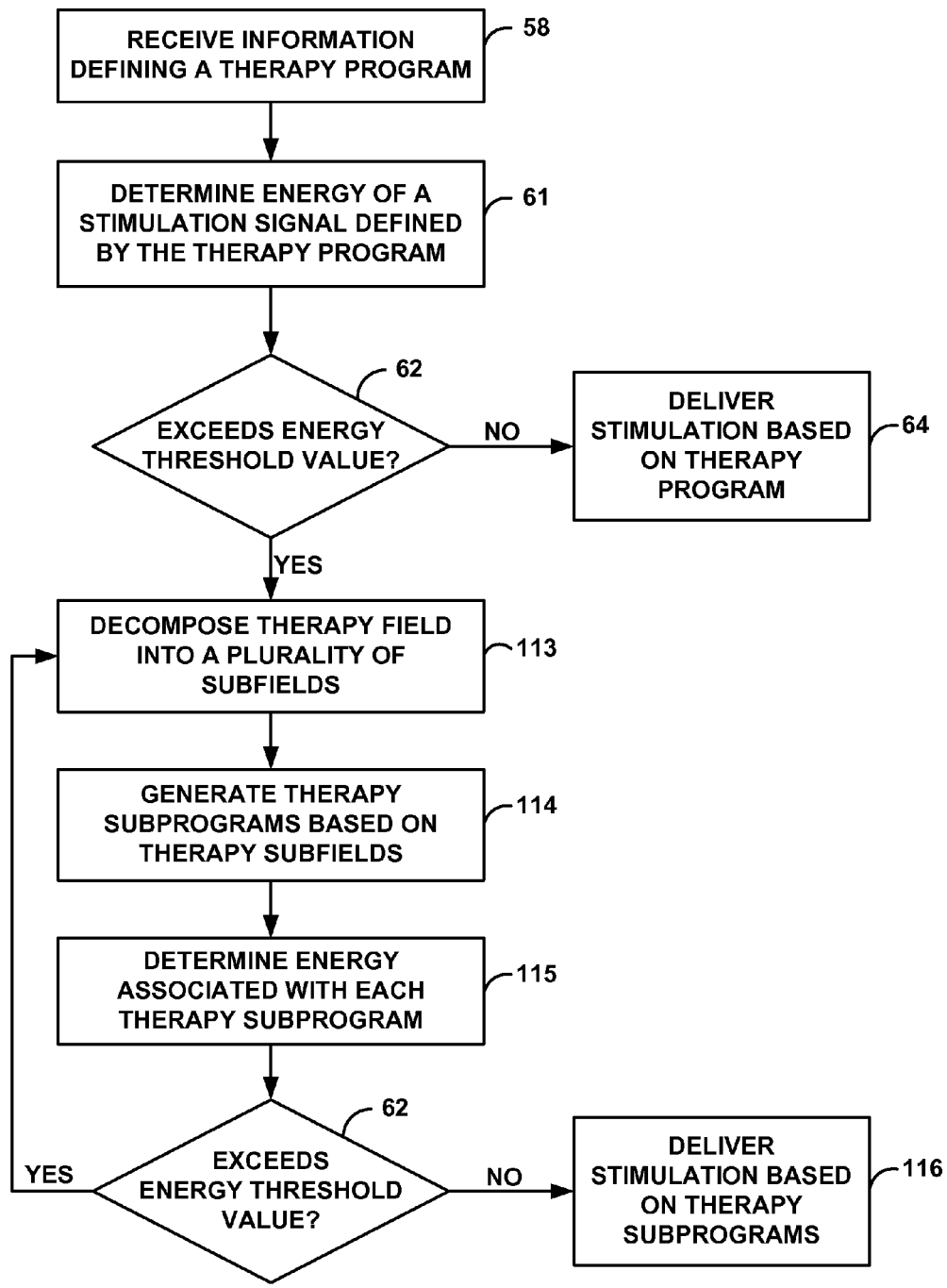
FIG. 9 is a flow diagram illustrating an example technique for decomposing a therapy field into a plurality of therapy subfields.

FIG. 9 is a flow diagram illustrating an example technique for determining whether to decompose a therapy field into a plurality of therapy subfields based on a comparison between an energy associated with the therapy program and a threshold value. As with the technique shown in FIG. 4, processor 90 may receive information that defines a therapy program (58). For example, processor 90 may receive a signal from IMD 14 or another device via telemetry interface (FIG. 6), where the signal indicates the therapy program, or processor 90 may select a therapy program from memory 92 (FIG. 6). As another example, processor 90 may receive the information as user input via user interface 88. In some examples, the information defining a therapy program may include input from a user defining and manipulating a desired therapy field (e.g., via drawing or otherwise drawing) via user interface 88 of programmer 20, e.g., as described in U.S. Pat. No. 7,822,483 to Stone et al. and U.S. Pat. No. 8,380,321 to Goetz et al. In other examples, the information defining a therapy program may include input from a user selecting appropriate structure of the anatomical region to stimulate, e.g., as described in U.S. Pat. No. 7,822,483 to Stone et al. and U.S. Pat. No. 8,380,321 to Goetz et al.

Energy calculator 98 of programmer 20 may calculate the energy associated with the stimulation signal defined by the therapy program (61). For example, energy calculator 98 may multiply the duration of the electrical stimulation signal defined by the therapy program with the amplitude of the electrical stimulation signal. If the information defining the therapy program includes input from a user defining or drawing a therapy field via user interface 88, prior to calculating an energy associated with the stimulation signal (61), processor 90 may determine the therapy parameter values associated with the clinician-defined therapy field. For example, processor 90 may reference instructions stored within memory 92 for generating stimulation fields and stimulation parameters from the therapy field. These instructions may include a set of equations needed to characterize brain tissue and interpret stimulation field dimensions. In some examples, as described in U.S. Pat. No. 8,380,321 to Goetz et al., processor 90 may determine the dimensions of the therapy field (e.g., a stimulation field) to create a 3D vector field identifying the distances from the implanted lead that stimulation may reach. Processor 90 may use a 3D vector field with an equation approximating electrical current propagation within the tissue of patient 14. In the case of stimulation delivery by stimulation pulses, the resulting data determines the electrode combination, voltage and current amplitudes, pulse rates, and pulse widths needed for reproducing the therapy field within patient 14. In other examples, processor 90 may interpret density of tissue in imaging data (e.g., CT, MRI, x-ray, fluoroscopy, and the like) to more precisely approximate the stimulation parameters.

In other examples, processor 90 may utilize stimulation templates to determine the stimulation parameters that are associated with the therapy field defined by the user. A stimulation template may be a volumetric stimulation field defined by stimulation parameters. Processor 90 may include a certain number of stimulation templates that are used to automatically generate stimulation parameters that best fit a user defined therapy field.

Processor 90 compares the determined energy of the stimulation signal defined by the therapy program with the energy threshold value 100 stored in memory 92 (62). As with the previous examples, energy threshold value 100 may be the value of the maximum energy of a stimulation signal that IMD 14 may generate or the maximum energy of one channel of IMD 14 if IMD 14 is a multichannel stimulator. The maximum energy may be the maximum energy at the time IMD 14 is implanted or the expected maximum energy output of IMD 14 after some predetermined amount of time, such as the expected life of IMD 14.

If the determined energy of a stimulation signal defined by the therapy program is less than the energy threshold value 100 (62) (or, in some cases, equal to the energy threshold value), processor 90 may control IMD 14 to generate and deliver therapy to patient 12 based on the therapy program defining the stimulation signal (64). For example, processor 90, with the aid of telemetry interface 94, may transmit the therapy program to IMD 14. Processor 90 may transmit the therapy parameter values or an indicator (e.g., an alphanumeric indicator) associated with the therapy program and processor 24 of IMD 14 may retrieve the therapy parameter values from memory 26 of IMD 14 based on the indicator. IMD 14 may then deliver therapy to patient 12 based on the therapy program.

If the determined energy is greater than (or, in some cases, equal to) the energy threshold value 100 (62), parameter generator 101 of programmer 20 may modify the therapy program to decompose the therapy field defined by the therapy program into a plurality of therapy subfields (113). As described above, the therapy field may be a stimulation field, electrical field, or activation field. Parameter generator 101 may generate therapy subprograms that define therapy parameter values for generating the therapy subfields (114). Energy calculator 98 may determine the energy associated with the stimulation signal defined by each therapy subprogram (115). For example, for each therapy subprogram, energy calculator 98 may multiply the duration of the electrical stimulation signal defined by the therapy subprogram with the amplitude of the electrical stimulation signal defined by the therapy subprogram.

For each therapy subprogram, processor 90 may compare the determined energy with the energy threshold value 100 (62). If the energy associated with each therapy subprogram is less than the energy threshold value (or, in some cases, equal to the energy threshold value), processor 90 may control IMD 14 to deliver therapy according to the therapy subprograms (116). That is, if the therapy subprograms are each associated with an energy less than the energy threshold value 100, processor 90 may transmit the therapy subprograms to IMD 14. In some examples, the therapy subprograms may be stored as a group with memory 26 of IMD 14 and/or memory 92 of programmer 20.

On the other hand, if the energy associated with each therapy subprogram is greater than the energy threshold value (or, in some cases, equal to the energy threshold value), processor 90 may continue decomposing the therapy field into subfields, such as by decomposing previously-generated subfields into small subfields associated with lower energies. Subfields may be associated with lower energies if, for example, IMD 14 requires less energy to generate and deliver stimulation signals to generate the therapy subfield, e.g., because the therapy subprogram has a smaller amplitude and signal duration.

FIG. 10A is a schematic illustration of an example of therapy field 118 that is generated when IMD 14 delivers electrical stimulation therapy to patient 12 according to a therapy program via electrodes 120A-120H (collectively referred to as "electrodes 120") of lead 122. Electrodes 120 may each be any suitable type of electrode, such as a ring electrode, segmented electrode or partial ring electrode. Lead 122 is one example of a lead. In other examples, lead 122 may have any suitable number of electrodes in other configurations (e.g., in a complex electrode array). Therapy field 118 may be, for example, a stimulation field, electrical field, or activation field.

In the example shown in FIG. 10A, the energy associated with the therapy program that results in therapy field 118 exceeds the energy threshold value 100 (or 36). As described with respect to FIG. 9, parameter generator 101 of programmer 20 may decompose therapy field 118 into a plurality of subfields, where the energy associated with each one of the subfields is less than the threshold energy value 100. The energy associated with each subfield may be, for example, an energy required to generate the stimulation signal defined by the therapy subprogram that generates the respective therapy subfield.

In some examples, therapy field 118 may be decomposed into two therapy subfields 124A, 124B, as schematically shown in FIG. 10B. An energy associated with each of the therapy subfields 124A, 124B is less than the threshold energy value 100, and is less than the energy associated with therapy field 118. The energy associated with therapy field 118 and therapy subfields 124A, 124B may be determined based on the therapy parameter values, such as the voltage or current amplitude and the signal duration, of the therapy program that IMD 14 delivers therapy in order to generate the respective field 118, 124A or 124B. In some cases, the sum of the energies of therapy subfields 124A, 124B is less than or equal to the energy associated with therapy field 118, while in other examples, the sum of the energies of therapy subfields 124A, 124B is greater than or equal to the energy associated with therapy field 118.

The therapeutic effect on patient 12 resulting from therapy delivery via therapy subfields 124A, 124B may be substantially similar to the therapeutic effect on patient 12 that results when IMD 14 delivers therapy via therapy field 118. In some examples, the total volume defined by the sum of the volumes of therapy subfields 124A, 124B may be within a particular percentage of the volume of the original therapy field 118, such as about 80% to about 150% of the volume of therapy field 118, such as about 90% to about 125% or about 95% to about 105%. Other percentages are contemplated. For example, the volumes of therapy subfields 124A, 124B may be up to 99.99% of the volume of therapy field 118, so long as the energy associated with each therapy subfield 124A, 124B is less than the energy threshold value 100.

In some examples, the total volume of therapy subfields 124A, 124B may substantially exceed or equal the volume of the original therapy field 118 (FIG. 10A), or may be less than the volume of the original therapy field 118. Accordingly, if therapy field 118 and therapy subfields 124A, 124B are stimulation fields or electrical fields, therapy subfields 124A, 124B may cover a particular percentage of the same volume of tissue of patient 12 as therapy field 118, such as about 80% to about 150%, about 90% to about 125% or about 95% to about 105%. If therapy field 118 and therapy subfields 124A, 124B are activation fields, therapy subfields 124A, 124B may substantially activate similar neurons as therapy field 118, such as about 80% to about 100% of the same neurons as therapy field 118, e.g., about 90% to about 110% or about 95% to about 105% of the same neurons as therapy field 118.

Parameter generator 101 of programmer 20 may modify the therapy program that defined therapy field 118 to define therapy subprograms that include therapy parameter values that generate therapy subfields 124A, 124B when IMD 14 delivers therapy according to the therapy subprograms. In one example, parameter generator 101 generates a plurality of subprograms where each one of the plurality of subprograms only activates a subset of the electrodes activated by the original therapy program. For example, parameter generator 101 may modify the electrode combination defined by the therapy program, which defines the electrodes 120 that are activated during therapy delivery according to the therapy program. In the example shown in FIG. 10A, the therapy program resulting in therapy field 118 selected electrodes 120A and 120H as active electrodes, and assigned polarities to electrodes 120A, 120H. In particular, the therapy program defined electrode 120A as an anode and electrode 120H as a cathode.

When IMD 14 delivers electrical stimulation according to the other therapy parameter values of the therapy program, such as the voltage or current amplitude and signal duration, electrical current flows from electrode 120H to electrode 120A and therapy field 118 is generated. Parameter generator 101 may modify the original therapy program and generate a first therapy subprogram that selects electrodes 120A and 120E as active electrodes, where electrode 120A is am anode and electrode 120E is a cathode. When IMD 14 delivers electrical stimulation according to the first therapy subprogram, electrical current flows from electrode 120E to electrode 120A, thereby generating therapy subfield 124A.

The electrode combination of the first therapy subprogram generally defines the location of the therapy subfield 124A substantially along a longitudinal axis of lead 122. In order to define the volume of therapy subfield 124A, processor 90 may select the therapy parameter values of the first therapy programs that define the intensity of stimulation, such as the voltage or current amplitude, signal duration or frequency. In some examples, processor 90 may select the therapy parameter values of therapy subfields 124A such that therapy subfield 124A has a volume that is within a particular range of therapy field 118, such as about 40% to about 60% of the volume of therapy field 118, although other percentages are contemplated. The clinician may select the range of volumes for therapy subfield 124A. Accordingly, the therapy parameter values of the first therapy subprogram (e.g., amplitude, pulse width or frequency) other than electrode combination may be selected based on the volume of therapy field 118. In one example, the therapy parameter values of the first therapy subprogram other than electrode combination are substantially similar to the original therapy program. In other examples, the therapy parameter values may be selected such that the volume of therapy subfield 124A is approximately half of the volume of therapy field 118.

Parameter generator 101 of programmer 20 may generate a second therapy subprogram that results in therapy subfield 124B when IMD 14 delivers therapy to patient 12 according to the second therapy subprogram. In the example shown in FIG. 10B, parameter generator 101 selects electrode 120D as an anode of the electrode combination and electrode 120H as a cathode of the combination. The electrode combination of the second therapy subprogram generally defines the location of the therapy subfield 124B substantially along the longitudinal axis of lead 122. In order to define the volume of therapy subfield 124B, processor 90 may select the therapy parameter values of the second therapy program that defines the intensity of stimulation, such as the voltage or current amplitude, signal duration or frequency. For example, just as with therapy subfield 124A and the first therapy subprogram, in some examples, processor 90 may select the therapy parameter values of the second therapy subprogram such that therapy subfield 124B has a volume that is within a particular range of therapy field 118, such as about 40% to about 60% of the volume of therapy field 118. The clinician may select the acceptable range of volumes for therapy subfields 124A, 124B.

After therapy field 118 is decomposed into subfields 124A, 124B, energy calculator 98 of programmer 20 may determine the energy associated with subfields 124A, 124B. For example, energy calculator 98 may determine the energy associated with subfields 124A, 124B based on the pulse width and amplitude of the first and second therapy subprograms, respectively. If the energy associated with subfields 124A, 124B is less than energy threshold value 100, processor 90 may store the first and second therapy subprograms within memory 92 of programmer 20, transmit the first and second therapy subprograms to IMD 14 or both.

Processor 24 of IMD 14 may control stimulation generator 30 of IMD (FIG. 2) to generate and deliver therapy to patient 12 in accordance with the first and second therapy subprograms substantially simultaneously, if IMD 14 is a multichannel device and the energy threshold value 100 is the threshold value for each channel, or via an interleaved or alternating fashion. In one example of interleaved therapy delivery, each pulse or signal is delivered according to a different one of first or second therapy subprograms. The time period between each pulse or signal may be less than the duration of the carryover effect, such that patient 12 perceives a cumulative effect from therapy delivery according to the first and second therapy subprograms and generally cannot differentiate between the pulses or signals of the different therapy subprograms. Each subfield 124A, 124B may activate different tissue, and, accordingly, the group of therapy subprograms may maintain the stimulation rate defined by the original therapy program, as well as the coverage of the therapy field 118. The interleaving of therapy delivery according to the first and second therapy subprograms may help provide effective therapy in many cases, despite the sequential nature of the stimulation. In some examples, subfields 124A, 124B may partially overlap, as shown in FIG. 10B.

If the energy associated with therapy subfields 124A, 124B is greater than energy threshold value 100, processor 90 may initiate the decomposition of therapy subfields 124A, 124B into additional subfields, such as the four therapy subfields 126A-126D shown in FIG. 10C. Parameter generator 101 may modify the therapy program that defined the original therapy field 118 and generate therapy subprograms that define therapy subfields 126A-126D. In the example shown in FIG. 10C, parameter generator 101 generates a first therapy subprogram that defines therapy subfield 126A. In particular, parameter generator 101 selects electrode 120A as an anode and electrode 120B as a cathode of the electrode combination of the first therapy subprogram.

Parameter generator 101 may also generate a second therapy subprogram that defines therapy subfield 126B. In the example shown in FIG. 10C, parameter generator 101 selects electrode 120C as an anode and electrode 120E as a cathode of the electrode combination of the second therapy subprogram. Parameter generator 101 may also generate a third therapy subprogram that defines therapy subfield 126C, where the third therapy subprogram selects electrode 120E as a cathode and electrode 120G as an anode. In the example shown in FIG. 10C, the second and third therapy subprograms share a cathode. In addition, parameter generator 101 may generate a fourth therapy subprogram that defines therapy subfield 126D, where the fourth therapy subprogram defines electrode 120G as an anode and electrode 120H as a cathode. In the example shown in FIG. 10C, the third and fourth therapy subprograms share an anode.

Just as with therapy subfields 124A, 124B in FIG. 10B, processor 90 may select the therapy parameter values of the first, second, third, and fourth therapy subprograms such that a total volume of therapy subfields 126A-126D is within a clinician-selected range of therapy field 118, such as about 80% to about 150% of the volume of therapy field 118.

Based on the respective therapy subprogram, energy calculator 98 may determine the energy associated with each of therapy subfields 126A-126D and compare each determined energy to energy threshold value 100. If the energy of one or more of the therapy subfield 126A-126D exceeds energy threshold value 100, processor 90 may further decompose the respective therapy subfields 126A-126D into therapy subfields having smaller volumes. Alternatively, processor 90 may further decompose all of the therapy subfields 126A-126D into therapy subfields having smaller volumes, rather than just the therapy subfield that is associated with an energy that exceeds energy threshold value 100. If the energy of each therapy subfield 126A-126D does not exceed energy threshold value 100, processor 90 may transmit the subprograms to IMD 14. The first, second, third, and fourth therapy subprograms, which result in therapy subfields 126A-126D, may be stored as a therapy program group within memory 26 (FIG. 2).

Processor 24 of IMD 14 may control stimulation generator 30 to deliver therapy to patient 12 according to the therapy group including the first, second, third, and fourth therapy subprograms. If IMD 14 is a multichannel device and energy threshold value 100 is specific to each stimulation channel, stimulation generator 30 may deliver the therapy according to the first, second, third, and fourth therapy subprograms substantially simultaneously if IMD 14 via separate channels. In other examples, stimulation generator 30 may deliver the therapy according to the first, second, third, and fourth therapy subprograms on an interleaved or alternating basis. The stimulation signals according to each therapy subprogram in the therapy group may be spatially separated such that patient 12 perceives a cumulative effect from therapy delivery according to the subprograms and generally cannot differentiate between the pulses or signals of the different therapy subprograms. In this way, therapy delivery according to the therapy group including the first, second, third, and fourth therapy subprograms may generally maintain the physiological effects of therapy field 118. The first, second, third, and fourth therapy subprograms may be selected by stimulation generator 30 in any order, as long as stimulation generator 30 cycles through each therapy subprogram in the group.

As described above, processor 90 decomposed therapy field 118 into either two therapy subfields 124A, 124B or four therapy subfields 126A-126D. In other examples, processor 24 of IMD 14, processor 90 of programmer 20 or a processor of another device may decompose therapy field 118 into any suitable number of therapy subfields until the energy associated with each subfield is less than energy threshold value 100. Furthermore, in some examples, the clinician or another user may decompose therapy field 118 into a plurality of therapy subfields with the aid of a GUI, which is described below in reference to FIGS. 11-14.

Processor 90 of programmer 20 may determine the approximate volume and shape of therapy field 118 based on the therapy program via any suitable technique. In some examples, the clinician may select therapy field 118 during programming of IMD 14, as described in U.S. Pat. No. 8,380, 321 to Goetz et al. For example, during a programming session, a clinician may interact with user interface 88 (FIG. 6) to manually select and program particular electrodes of a lead via an electrode selection view, and adjust a stimulation field resulting from a particular electrode selection. Once the clinician has defined the one or more stimulation fields, programmer 20 may generate the stimulation parameter values associated with the stimulation fields selected by the clinician. The stimulation parameter values may be transmitted to IMD 14 or stored within memory 92 of programmer 20. Hence, user interface 88 of programmer 20 may permit a user to manually select electrode combinations and associated stimulation parameter values, or simply specify and manipulate a stimulation field in terms of size, direction and shape, in which case the programmer 20 or IMD 14 may automatically adjust electrode combinations and parameter values to approximate the desired stimulation field.

The stimulation field selected by a clinician during the programming of IMD 14 may be stored within memory 92 of programmer 20 or memory 26 of IMD 14 as an algorithmic model of a therapy field 118 that represents a therapy field that provides effective therapy to patient 12. That is, in some examples, user interface 88 may present a representation of one or more implanted leads and a representation of the patient anatomy proximate the implanted lead. The clinician may define a desired stimulation field over the representation of the patient anatomy, relative to the representation of the one or more implanted leads or relative to both the representation of the patient anatomy and the implanted leads. The clinician-defined stimulation field may be the algorithmic model of the therapy field 118 that provides efficacious therapy to patient 12. The clinician, processor 24 of IMD 14, processor 90 of programmer 20 or a processor of another device may decompose therapy field 118 into therapy subfields with the aid of the algorithmic model of therapy field 118.

Figure 11:
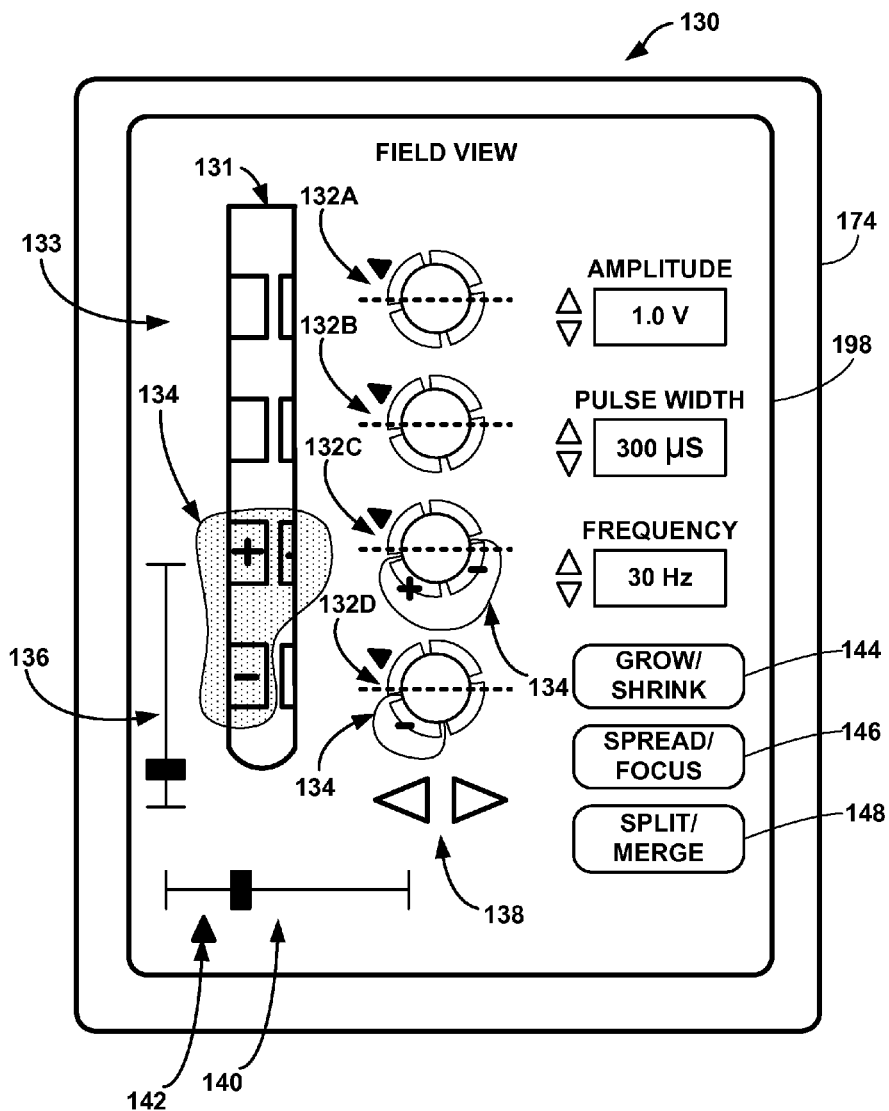
FIG. 11-14 illustrate example graphic user interfaces (GUIs) that may be presented on a display of a programming device in order to generate an algorithmic model of a therapy field and aid the decomposition of the therapy field into a plurality of subfields.

FIG. 11 illustrates a schematic representation of an example graphic user interface (GUI) 130 that may be presented on a display of programmer 20. By interacting with GUI 130, a user may generate an algorithmic model of an electrical stimulation field produced by a selected electrode combination. For example, the user may change the size, shape or position of the field using graphical input media such as cursor or stylus control. In some examples, the user may be able to create a stimulation field in the field view and direct processor 90 of programmer 20 to generate stimulation parameter values that would best match the stimulation field. The generated electrical stimulation field may be stored as an algorithmic model of therapy field 118 and the stimulation parameter values may be stored as a therapy program.

GUI 130 illustrates lead 131, which includes a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead, e.g., as illustrated with lead 16 of FIG. 2. Another example of a simple electrode array geometry is a planar array of electrodes on a paddle lead.

Lead 131 includes four electrode "levels" at different axial positions along the length of the lead. Each level includes four electrodes generally arranged in a ring. However, the electrodes are non-contiguous with one another. The electrodes may be referred to as segmented electrodes or electrode segments. Each electrode is coupled to a respective electrical conductor within lead 131. Hence, lead 131 includes multiple electrical conductors, e.g., wires, cables or the like, that extend from the proximal end of the lead to respective electrodes to electrically couple the electrodes to electrical terminals associated with IMD 14.

Each electrode is positioned at a different angular position around the circumference of implantable lead 131, which has a generally circular cross-section in the example of FIG. 11. Each electrode is independently selectable so that stimulation energy can be delivered from the lead at different axial and angular positions. In some examples, lead 131 may include combinations of complex electrode array geometries and simple electrode array geometries. For example, ring electrodes that extend about the entire circumference of the lead may be used in combination with electrodes disposed at different axial and angular positions. Selective activation of the electrodes carried by lead 131 can produce customizable stimulation fields that may be directed to a particular side of lead 131 in order to isolate the stimulation field around a target anatomical region within patient 12.

GUI 130 illustrates multiple cross-sectional views 132A-132D and a side view 133 of lead 131 in alignment with corresponding electrode levels. In the example of FIG. 11, the user has selected an initial electrode combination, either manually or by selection for a set of electrode combinations provided by programmer 20, and the selected electrode combination is illustrated in GUI 130. GUI 130 presents a representation of a stimulation field 134 defined by the user and produced by the selected electrode combination, given stimulation parameter values selected by the user and general tissue characteristics stored within programming device 110. Stimulation field 134 may be, for example, an example of therapy field 118 (FIG. 10A).

The size and shape of stimulation field 134 may be established based on generic physical characteristics of human tissue and known physical characteristics of the electrodes of lead 131. In other words, stimulation field 134 displayed in the field view of GUI 130 may only be an approximation of what the stimulation field would be in tissue of a specific patient 12. However, in some examples, physical characteristics of the actual anatomical structure of patient 12 being treated may be used to generate stimulation field 134. This anatomical structure information may be presented to programmer 20 in the form of patient anatomical data generated by an imaging modality, such as CT, MRI, or any other volumetric imaging system and stored within memory 92 of programmer 20.

In the example that uses the patient anatomical data, stimulation field 134 may be similar to an electrical field model, which is discussed in detail with reference to FIGS. 13 and 15. For example, stimulation field 134 may rely on tissue impedance models, field propagation models, and the like. In some examples, stimulation field 134 may be a representation of an electrical field, current density, voltage gradient, or neuron activation, applied to a generic human tissue or the anatomy of patient 12. In addition, the clinician may be able to switch between any of these representations when desired.

The user may move stimulation field 134 up or down relative to a longitudinal axis of lead 131 within GUI 130 using vertical scroll bar 136 or some similar control device. As stimulation field 134 moves up or down in response to the user input, programmer 20 automatically selects appropriate electrode combinations to support the vertical movement of the stimulation field. For example, processor 90 may phase electrodes in and out as stimulation field 134 travels upward or downward, reducing the stimulation energy delivered from some electrodes as the stimulation field moves away from them, and increasing the stimulation energy delivered by other electrodes as the field moves toward them. Also, GUI 130 includes arrows 138 or similar input media that permit the user to transition between different electrode levels of the lead in cross-sectional views 132A-132D.

In addition, the user may rotate stimulation field 134 using horizontal scroll bar 140 or some similar control device. An arrow 142 may be provided next to horizontal scroll bar 140 to indicate the orientation of lead 131 relative to an anatomical structure. In addition, arrows may be provided in respective cross-section views 132A-132D to maintain orientation. As the user rotates stimulation field 134, processor 90 of programmer 20 may automatically select appropriate electrode combinations to support the rotational movement of the stimulation field 134. As in the case of vertical movement, rotational movement of stimulation field 134 may be accomplished by gradually reducing the stimulation energy delivered to some electrodes as the stimulation field rotates away from them, and gradually increasing the stimulation energy delivered to other electrodes as the stimulation field rotates toward them. Side view 133 and cross-sectional views 132A-132D permit the user to observe movement of stimulation field 134 from both an axial perspective and a rotational perspective.

Movement of stimulation field 134 within GUI 130 using scroll bars 136, 140 or similar input media permits the user to evaluate different field positions without the need to manually select electrodes and manually enter parameter values. Instead, processor 90 of programmer 20 automatically selects electrodes and parameter values in response to movement of stimulation field 134 by the user. Although scroll bars 136, 140 are illustrated as examples of input media for movement of stimulation field 134, other types of input media may be used. Examples include up/down arrows or side-to-side arrows, which may be presented on a touch screen or formed by buttons or keys on programmer 20.

As a further alternative to manipulating the stimulation field 134, the user may select stimulation field 134 within GUI 130 with a stylus, mouse, or other pointing device and drag the field upward, downward, or rotationally. In some examples, a mouse or other pointing device may support left or right click functionality to perform different operations relative to stimulation field 134. With a stylus, a first click on stimulation field 134 may initiate movement, dragging with the stylus directs movement, and a second click may terminate movement. In each case, processor 90 of programmer 20 responds to the specified movement by automatically adjusting the electrode combination and other stimulation parameter values to approximate the characteristics of stimulation field 134 presented by GUI 130. As the stimulation parameter values change, the size and shape of stimulation field 134 presented on the display change. Similarly, as the electrode combination changes in terms of polarity or electrode selection, the size, shape or direction of stimulation field 134 presented on the display changes.

In some examples, in order to generate a therapy program that results in stimulation field 134, processor 90 may utilize stimulation templates and select the best fitting stimulation template set to stimulation field 134. A stimulation template is a predetermined volumetric stimulation field that processor 90 may substantially match to a desired stimulation field 134 from the clinician. An algorithm for generating a therapy field model that utilizes one or more stimulation templates to generate stimulation parameter values that fit the user defined stimulation field may be less computationally intensive for processor 90 compared to an algorithm that references multiple equations or lookup tables to generate the stimulation parameter values. The stimulation template may be a representation of an electrical field or other electrical stimulation related characteristic, e.g., current density, voltage gradient, or neuron activation, applied to a generic human tissue. For stored stimulation templates, processor 90 may adjust the current amplitude or voltage amplitude to alter the size of the stimulation template to cover the desired stimulation field 134 from the user. Examples of stimulation templates are described in U.S. Pat. No. 8,380,321 to Goetz et al.

In addition to moving stimulation field 134, GUI 130 may permit the user to perform one or more operations that result in reconfiguration of stimulation field 134. For example, the user may click on a border, i.e., an outer perimeter, of stimulation field 134 presented by GUI 130, and drag it inward or outward to resize the stimulation field. Resizing by enlarging or shrinking stimulation field 134 in GUI 130 results in an increase or decrease in amplitude, pulse width or pulse rate of the stimulation energy. In some examples, enlarging or shrinking stimulation field 134 also may result in selection or de-selection of electrodes included in the existing electrode combination. In either case, processor 90 of programmer 20 adjusts the electrode combination and/or parameter values in response to the enlargement or shrinkage of stimulation field 134 by the user. In this way, a user may generate an algorithmic model of a therapy field by directly manipulating the stimulation field 134. Other field adjustment functions such as spread/focus button 146 and split/merge button 148 may be provided by GUI 130. In each case, the user changes stimulation field 134 by simply changing the representation of the stimulation field 134 presented on GUI 130, thereby avoiding the need to manually select electrodes and parameter values. The operation of the buttons 144, 146, and 148 is described in further detail in U.S. Pat. No. 8,380,321 to Goetz et al.

Processor 90 of programmer 20, processor 24 of IMD 14, a processor of another device, or a clinician, with the aid of a computing device, may decompose stimulation field 134 into a plurality of therapy subfields with the aid of GUI 130. While processor 90 of programmer 20 is primarily referred to throughout the description of FIGS. 11-14, in other examples, processor 24 of IMD 14, a processor of another computing device may perform any one or more of the techniques described herein. In one example, after selecting a desirable stimulation field 134, energy calculator 98 may determine an energy associated with stimulation field 134, as described above with respect to FIG. 9. If the therapy program is selected prior to determining stimulation field 134, energy calculator 98 may reference the stimulation parameter values of the therapy program.

If the therapy program is selected by first defining stimulation field 134, prior to determining the energy, processor 90 may determine the therapy parameters associated with stimulation field 134 and energy calculator 98 may determine the energy associated with stimulation field 134 based on the associated amplitude and signal duration values defined by the therapy program. As described above, processor 90 may determine the stimulation parameters associated with stimulation field 134 by, for example, determining the dimensions of stimulation field 134 to create a 3D vector field identifying the distances from the implanted lead 131 that stimulation may reach. Processor 90 may use a 3D vector field with an equation approximating electrical current propagation within the tissue of patient 14. In other examples, processor 90 may utilize stimulation templates to determine the stimulation parameters that are associated with stimulation field 134.

If processor 90 determines that the energy associated with stimulation field 134 exceeds (e.g., is greater than or equal to) a stored energy threshold value 100, processor 90 may prompt the clinician to modify stimulation field 134 within GUI 130 and select a plurality of therapy subfields with the aid of GUI. In other examples, processor 90 may automatically decompose stimulation field 134 into a plurality of therapy subfields with the aid of GUI 130 and present the plurality of therapy subfields to a user, such as the clinician, for approval.

Figure 12:
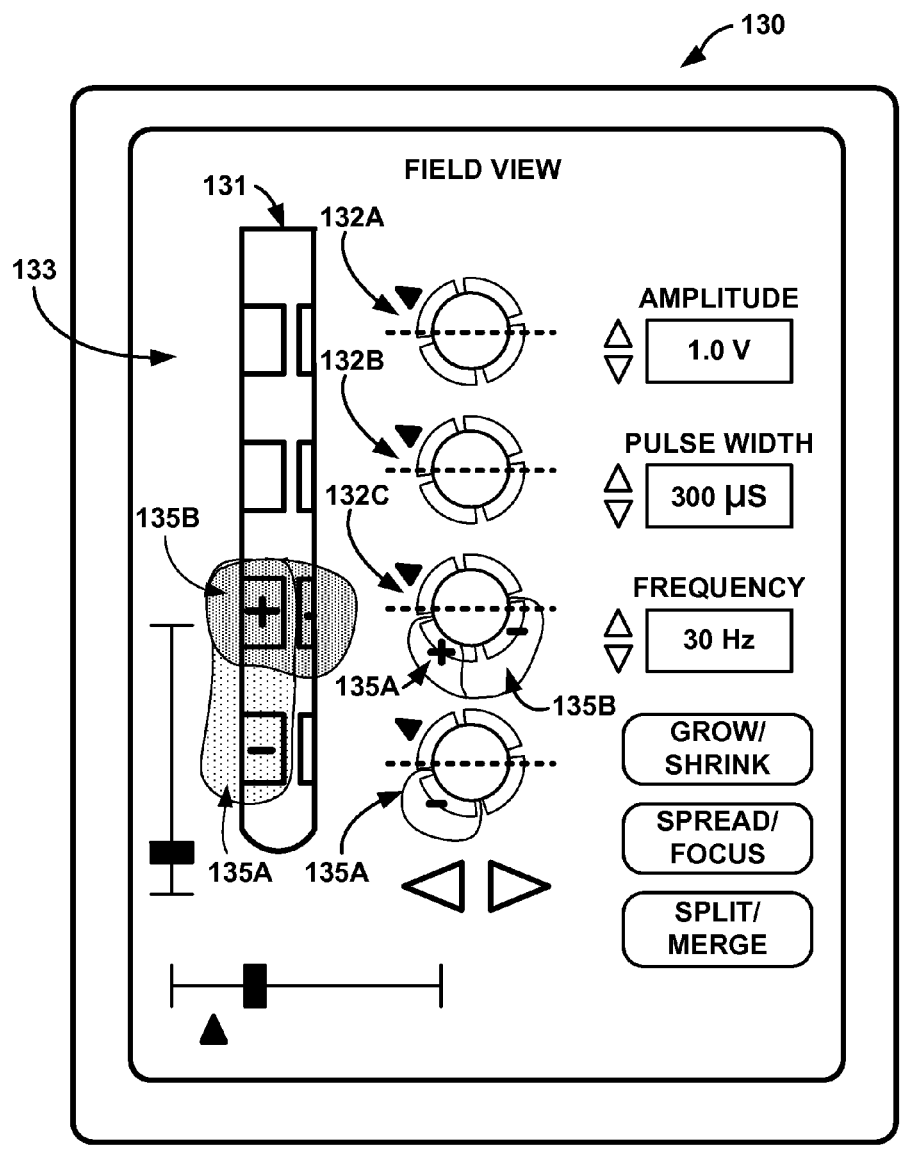

FIG. 12 illustrates an example of GUI 130 presenting stimulation subfields 135A, 135B that processor 90 automatically generated based on stimulation field 134. In one technique for decomposing stimulation field 134 into two or more stimulation subfields, processor 90 may split stimulation field 134 along a longitudinal axis of lead 131 or, as shown in FIG. 12, along a lateral axis that is substantially perpendicular to the longitudinal axis of lead 131, thereby resulting in two subfields 135A, 135B. If an energy associated with the subfields 135A, 135B exceeds the threshold value 100, processor 90 may further decompose the subfields 135A, 135B along the same or a different axis relative to lead 131. However, in some cases, depending on the available electrodes for selection 131, further decomposition of subfields 135A, 135B may not be possible. Electrode availability permitting, processor 90 may iteratively split the stimulation subfields 134 until an energy associated with the therapy subfields is less than the threshold value 100. In some cases, processor 90 may selectively decompose specific subfields, rather than all of the subfields. For example, processor 90 may selectively decompose stimulation subfield 135A into two or more subfields, and maintain stimulation subfield 135B as a single subfield.

In the example shown in FIG. 12, the total volume of stimulation subfields 135A, 135B is greater than the volume of stimulation field 134 because stimulation subfields 135A, 135B substantially overlap around the electrode level shown in the cross-sectional view 132C. However, the energy associated with stimulation subfield 135A is less than the energy associated with threshold value 100, and the energy associated with stimulation subfield 135B is less than the energy associated with threshold value 100.

Processor 90 may present stimulation subfields 135A, 135B to the user for approval. Upon approval by clinician, processor 90 may store the therapy parameter values associated with stimulation subfields 135A, 135B within memory 92 or may transmit the therapy subprograms to IMD 14. Processor 90 may determine the therapy parameter values associated with stimulation subfields 135A, 135B using any suitable technique, such as the techniques described above for determining the therapy parameter values for achieving stimulation field 134. In one example, the user or processor 90 generates a first therapy subprogram associated with stimulation subfield 135A with the aid of stimulation templates, and select the best fitting stimulation template set to stimulation subfield 135A. Processor 90 may generate a therapy subprogram comprising the stimulation parameters that define the stimulation template that most closely matches stimulation subfield 135A. In some examples, the user or processor 90 may need to select multiple stimulation templates in order to closely match stimulation subfield 135A. In such examples, processor 90 may generate a therapy subprogram comprising the sets of stimulation parameters that define the plurality of stimulation templates. Similarly, the clinician or the processor 90 may generate a second therapy subprogram associated with stimulation subfield 135B with the aid of stimulation templates, and select the best fitting stimulation template set to stimulation subfield 135B.

In other examples, processor 90 of programmer 20 may generate an algorithmic model of an electrical field or an algorithmic model of an activation field, and processor 90 or a clinician with the aid of programmer 20, may decompose the electrical field model or the activation field model into a plurality of therapy subfields and generate therapy subprograms based on the therapy subfields.

Figure 13:
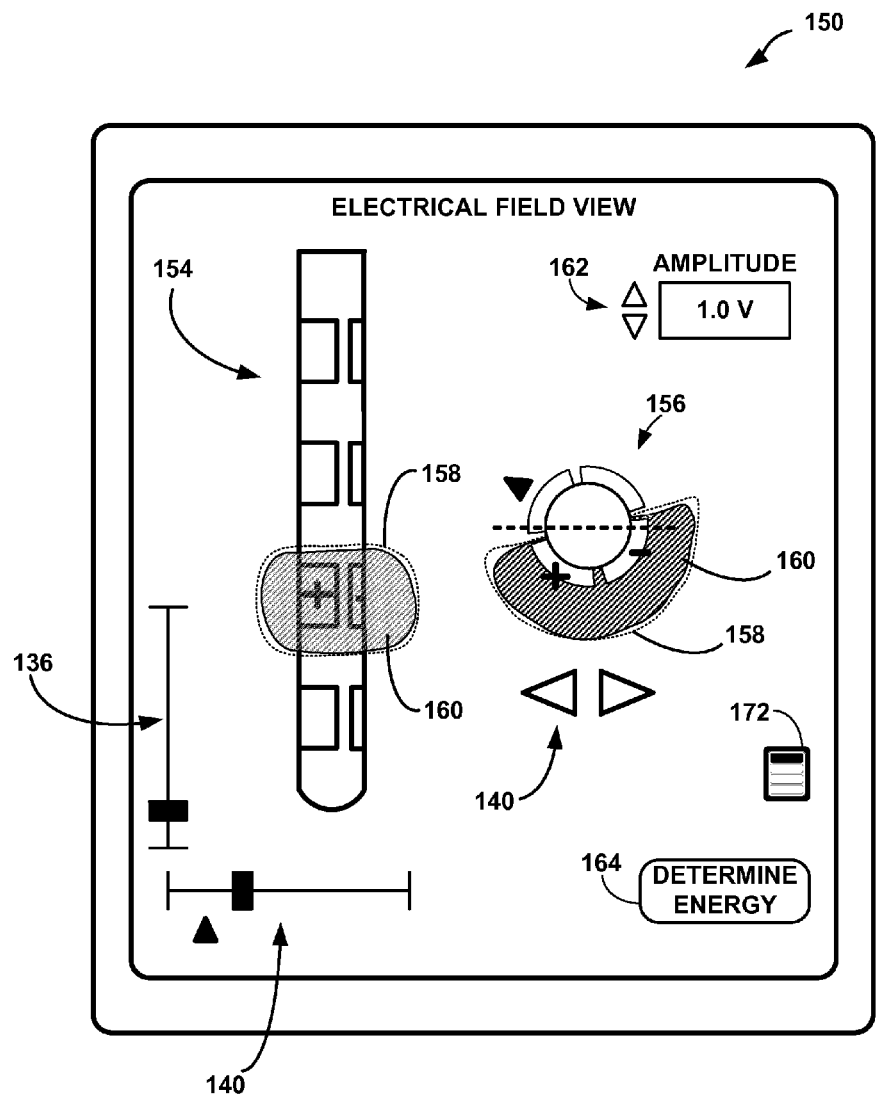
Figure 14:
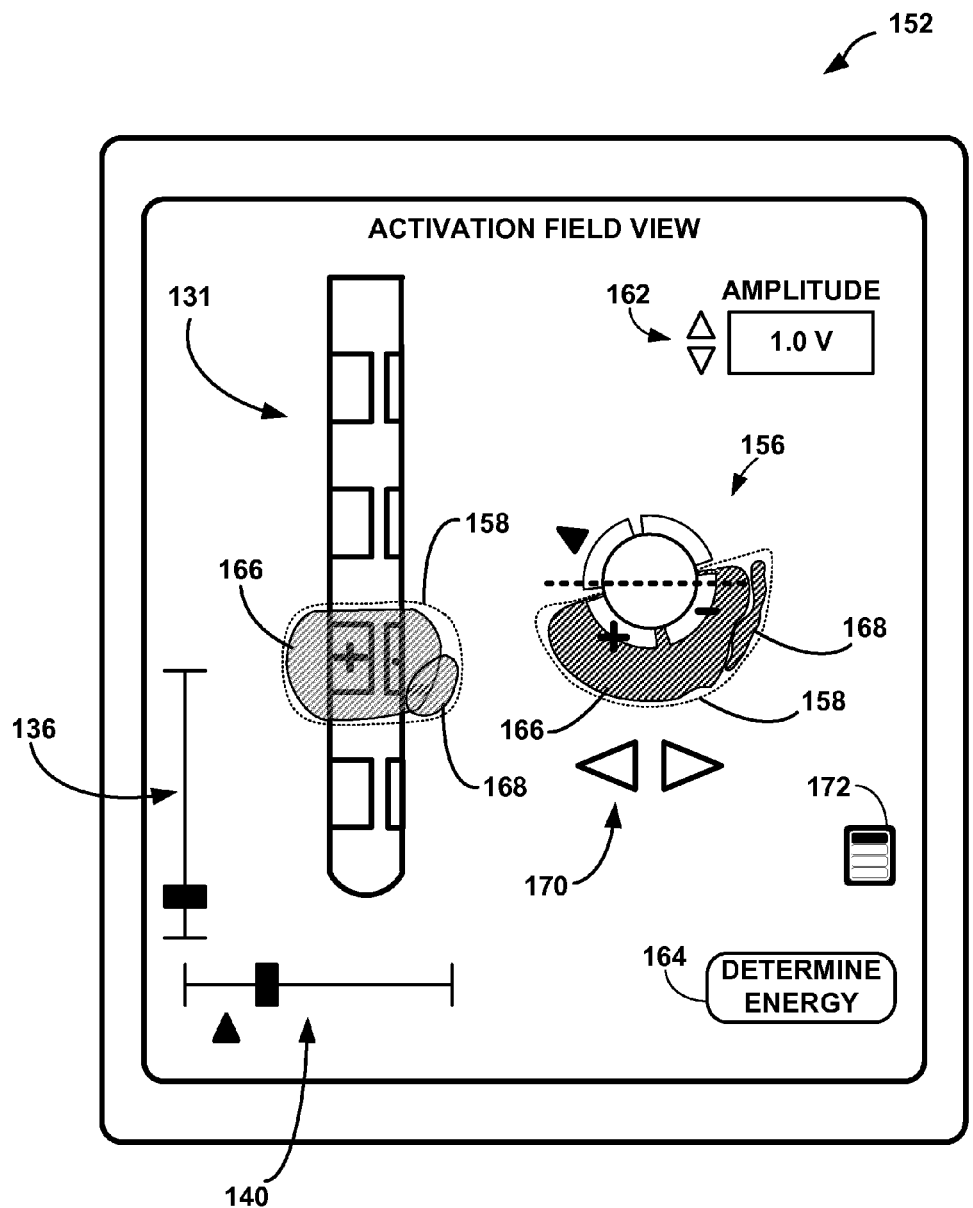

FIGS. 13 and 14 are schematic diagrams illustrating example GUIs 150, 152 that present electrical field models and activation field models, respectively, to a user. FIG. 13 illustrates an example GUI 150 that displays a stimulation field view to the user via a display of programmer 20. GUI 150 displays side view 154 and cross-sectional view 156 of implanted lead 131, and the user defines stimulation field 158 on the side and cross-sectional views, e.g., using the techniques described above with respect to FIG. 11. Processor 90 of programmer 20 may generate stimulation parameter values for therapy based on the selected stimulation field 158 and generate an electrical field model 160, which estimates an electrical field that results from therapy delivery according to the stimulation parameter values associated with the selected stimulation field 158. In GUI 150, electrical field model 160 is displayed as an electrical field within the outer boundaries of stimulation field 158. In other examples electrical field model 160 may be a representation of another electrical stimulation related characteristic, e.g., current density, or voltage gradient. In addition, the clinician may be able to switch between any of these representations when desired.

Electrical field 160 represents where the electrical current will propagate from the implanted lead 131 within patient 12, as tissue variation of the tissue proximate to lead 131 may change the electrical current propagation from the lead in some directions. The variations in electrical field propagation may affect the ability of the therapy to actually treat a desired structure or cause a side effect. The horizontal and axial views of electrical field model 160 illustrated in FIG. 13 are two-dimensional (2D) slices of a volumetric electrical field model generated by processor 90. Processor 90 utilizes an algorithm to generate electrical field model 160. In one example, the algorithm takes the patient anatomy data with electrical field model equations that define electrical current propagation into consideration. Accordingly, if the algorithmic model of the baseline therapy field includes electrical field 160, processor 90 may implement an algorithm that applies electrical field model equations that define how the electrical field propagates away from an origin location. The electrical field model equations may be specific to patient 12. The electrical field equations require the physical tissue characteristics of the tissue adjacent lead 131. From this information, processor 90 is able to generate the estimated electrical field 160 that will be produced in therapy.

Electrical field 160 may differ from the selected stimulation field 158 because processor 90 generates stimulation field 158 using an algorithm that only considers general tissue characteristics, which are not specific to patient 12. In other examples, the electrical field equations may utilize matrices or other mathematical model of the electrical field. In this manner, electrical field 160 can be estimated and modeled for the user. Accordingly, the user may be able to increase or decrease the amplitude of the stimulation parameter values with amplitude interface 162 in order to change the size and possibly shape of electrical field 160 or directly manipulate electrical field 160. If the user is satisfied with electrical field 160, the user may select the determine energy button 164 to determine whether the energy associated with the therapy program that results in electrical field 160 exceeds energy threshold value 100 (or, in some cases, is greater than the threshold energy value 100). If the energy does not exceed threshold value 100, processor 90 may transmit the stimulation parameter values of the therapy program to IMD 14.

If the energy exceeds threshold value 100, processor 90 may notify the user that decomposition of electrical field 160 into two or more electrical subfields is desirable. The user may then interact with GUI 150 to define the electrical subfields that have a smaller volume than electrical field 160. The user may, for example, select subfields that cover the target anatomic regions of patient 12 that the user deems important to the therapeutic efficacy, e.g., based on past experience or prior test results. Processor 90 may then generate the therapy parameter values that may achieve the user-defined electrical subfields, e.g., using the patient anatomy data and electrical field model equations that define electrical current propagation. These therapy parameter values may define therapy subprograms. Alternatively, processor 90 may notify the user that decomposition of electrical field 160 is desirable, and automatically decompose electrical field 160 into two or more electrical subfields. For example, processor 90 may split electrical field 160 along a longitudinal axis of lead 131. Again, processor 90 may generate the therapy parameter values that may achieve the processor-selected electrical subfields.

FIG. 14 is similar to FIG. 13 and illustrates an example GUI 152 that displays an activation field view to the user via a display of programmer 20. From the defined stimulation field 158 on the side view 154 and cross-sectional view 156, processor 90 of programmer 20 may generate stimulation parameter values for therapy and generates an activation field model based upon the electrical field model 160 of FIG. 13 and a neuron model that estimates which neurons within the electrical field model will be activated by the voltage of the electrical field during therapy. The neuron model may be a set of equations, a lookup table, or another type of model that defines threshold action potentials of particular neurons that make up the anatomical structure, as defined by the patient anatomy data, affected by the electrical field 160. If the voltage or current amplitude of the electrical field 160 is above the threshold of any neuron within the electrical field, that neuron will be activated, e.g., cause a nerve impulse. The activation field model is displayed as activation fields 166 and 168 within stimulation field 158.

Activation fields 166 and 168 of the activation field model indicate to the user where neurons around the lead will be activated from the stimulation therapy. Due to changes in electrical current propagation and voltage thresholds to activate a neuron, the activation of neurons may vary with the location of tissue around the lead. Some neurons may activate further from the lead with smaller voltages while other neurons may only be activated close to the lead because of a high voltage threshold. These differences in neurons may account for separate activation fields 166 and 168 within a contiguous stimulation field 158.

The user may manipulate activation fields 166, 168 within GUI 152, such as to decompose activation fields 166, 168 into activation subfields. For example, the user may increase or decrease the size and/or shape of activation fields 166 and 168 by changing the amplitude with amplitude adjustment interface 162 or directly manipulate the activation fields to automatically modify the stimulation parameter values. Once the user is satisfied with activation fields 166, 168, the user may select determine energy button 164 and energy calculator 98 may determine the energy associated with activation fields 166, 168. In other examples, determine energy button 164 may be an "accept field" button, and energy calculator 98 may automatically determine the energy associated with activation fields 166, 168 upon activation of the button 164 by a clinician.

If the energy is not greater than the threshold value 100, processor 90 may transmit the stimulation parameter values of the therapy program to IMD 14. If the energy exceeds the threshold value 100, processor 90 may notify the user that decomposition of at least one of the activation fields 166, 168 into two or more activation subfields is desirable. The user may then interact with GUI 152 to define the activation subfields that have a smaller volume than at least one of activation fields 166, 168. The user may, for example, select subfields that cover the target anatomic regions of patient 12 that the user deems important to the therapeutic efficacy, based on past experience or prior test results. Processor 90 may then generate the therapy subprograms that may achieve the user-defined activation subfields, e.g., using the patient anatomy data, electrical field model equations that define electrical current propagation, and the neuron model.

In other examples, processor 90 may notify the user that decomposition of at least one of activation subfields 166, 168 is desirable, and automatically decompose at least one of activation subfields 166, 168 into two or more activation subfields. For example, processor 90 may split electrical field 160 in along a longitudinal axis of lead 131. However, because the activation fields 166, 168 depend upon the neuron model, the differences in neurons within the tissue proximate to the implanted lead 131 may account for noncontinuous activation subfields. Again, processor 90 may generate the therapy parameter values that may achieve the processor-selected activation subfields.

Figure 15:
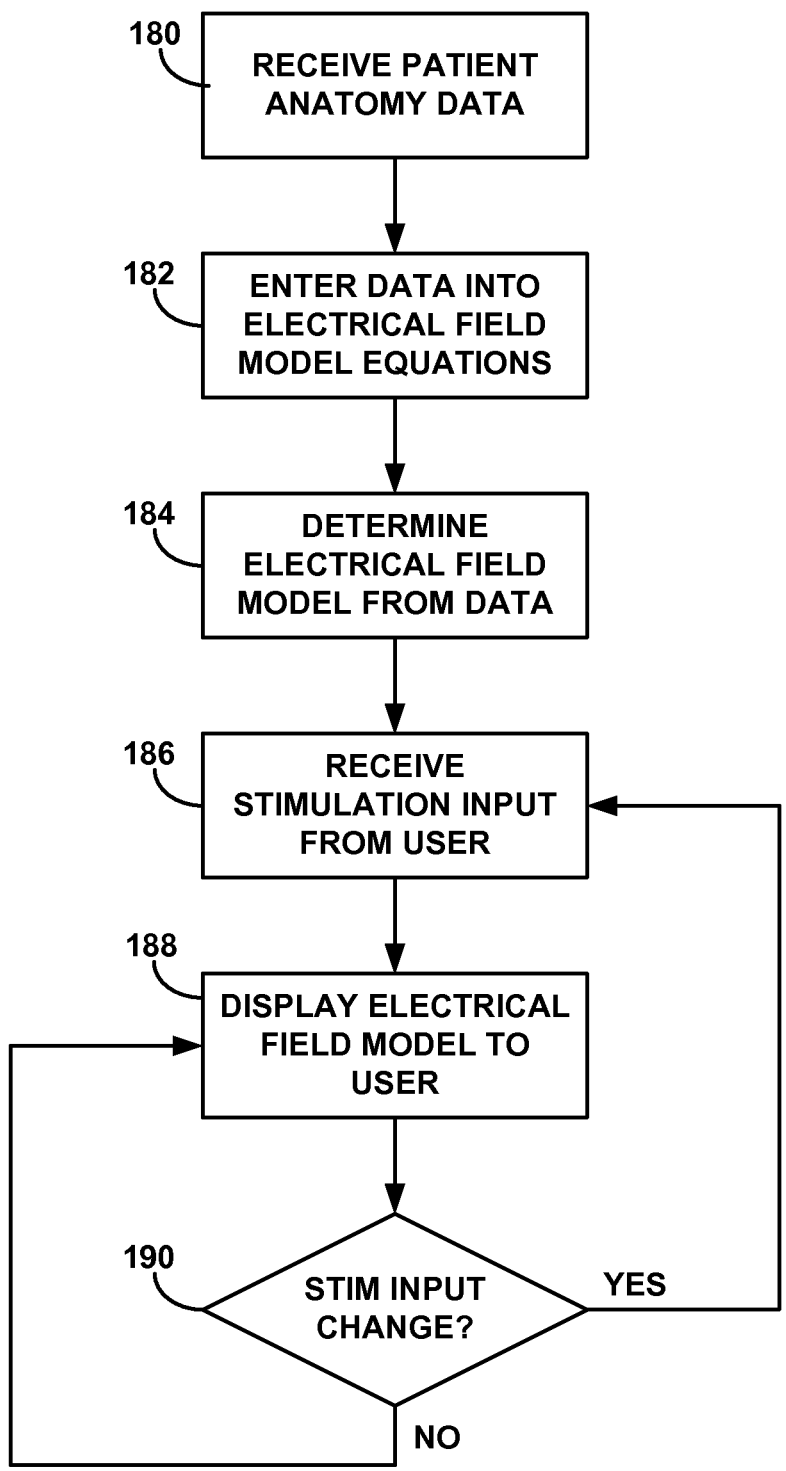
FIG. 15 is a flow diagram illustrating an example technique for determining and displaying an electrical field model.

FIG. 15 is a flow diagram illustrating an example technique for generating and displaying electrical field model 160 (FIG. 13), which is based on a stimulation field 158. Stimulation field 158 may be determined based on input by a clinician and/or automatically generated by processor 90 of programmer 20 in response to stimulation parameter values selected by the clinician. As shown in FIG. 15, processor 90 receives patient anatomy data necessary for creating an electrical field (180), which may include an anatomical image of the target tissue site of patient 12, a reference anatomical image, which may not be specific to patient 12, an anatomical atlas indicating specific structures of the patient's anatomy or a map of the tissue characteristics (e.g., conductivity or density) adjacent to the one or more implanted leads (e.g., leads 16A, 16B). As previously described, the patient anatomy data may be created based on a medical imaging technique, such as, but not limited to, computed tomography and magnetic resonance imaging. Processor 90 may store the patient anatomy data within memory 92 (FIG. 6).

Processor 90 may enter the patient anatomy data in stored electrical field model equations or equation sets to satisfy anatomical variable (182). Processor 90 may determine the electrical field model from the data and equations (184). Once processor 90 receives stimulation input from a user defining the stimulation field, e.g., via user interface 88 (186), the electrical field may be displayed to the user via a display of programmer 20 (188). In some cases, processor 90 may receive an indication change in the stimulation input from a user (190), and the modified electrical field model may be presented to the user (188). The algorithmic model of the electrical field model displayed to the user (188).

Figure 16:
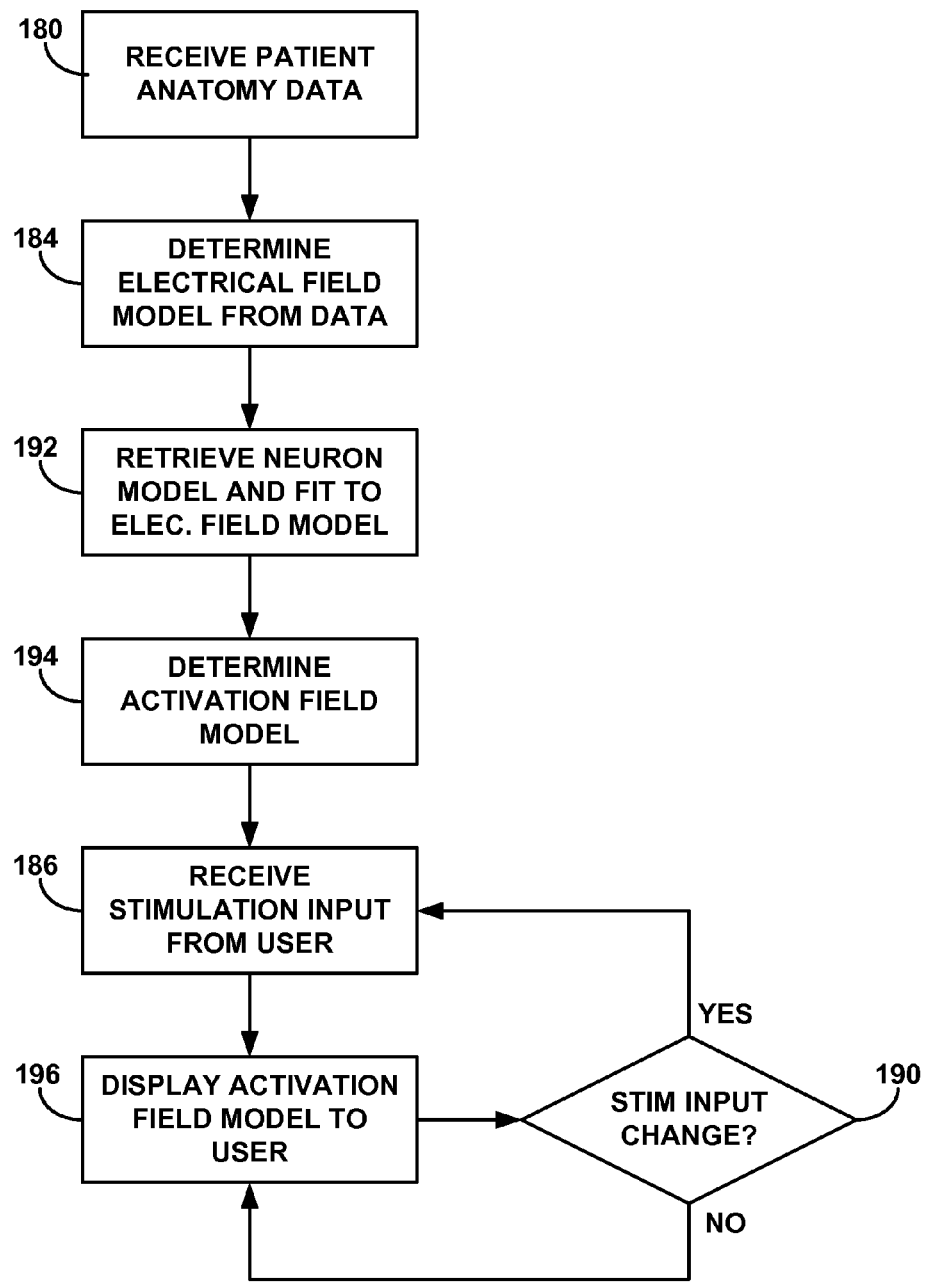
FIG. 16 is a flow diagram illustrating an example technique for determining and displaying an activation field model.

FIG. 16 is a flow diagram illustrating an example technique for determining and displaying the activation field model of defined stimulation. As shown in FIG. 17, processor 90 receives patient anatomy data indicative of the anatomy of patient 12 (180) and determines the electrical field model from the patient anatomy data (184). Processor 90 retrieves a neuron model from memory 92 (FIG. 6) and fits the neuron model to the electrical field model (192). Processor 90 may determine the activation field model based upon the electrical field model and neuron model (194).

Processor 90 may receive stimulation input from a user defining the stimulation field, e.g., via user interface 88 (186). Processor 90 may present the resulting activation field model to the user via a display of programmer 20 (196). If the clinician desires to change the stimulation input (190), processor 90 may receive user input from the clinician via user interface 88, where the input indicates a modification to the previous stimulation input (186). In some cases, processor 90 may receive an indication change in the stimulation input from a user (190), and the modified electrical activation field model may be presented to the user (196).

In some examples, GUIs 130 (FIG. 12), 150 (FIG. 13), and 152 (FIG. 15) may include a representation of anatomical regions proximate to the target tissue site for therapy delivery in addition to the lead icon 131. The representation of the target anatomical region may be an actual image of the patient's tissue produced with MRI, CT, or another imaging modality, or may be an atlas that is representative of the general anatomical structure of the target tissue site, and may not be specific to patient 12. The representation of the relevant anatomical region for the therapy delivery may be useful for determining whether therapy subfields generated based upon a therapy field are acceptable, e.g., whether the therapy subfields cover the same target anatomical structure as the therapy field. This may be particularly important when the target tissue site is within the brain of patient 12.

In addition, in some examples, GUIs 130 (FIG. 12), 150 (FIG. 13), and 152 (FIG. 15) may present therapy fields within a 3D environment. Although FIGS. 11-14 2D views of leads, in other examples, a user interface may present a 3D view of one or more leads and the associated electrical field and activation fields may be displayed relative to the 3D views of the leads.

The techniques described in this disclosure, including those attributed to processors 24 and 90, energy calculators 34 and 98, parameter generators 38 and 101, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable storage medium such as RAM, ROM, NVRAM, EEPROM, FLASH memory, magnetic data storage media, optical data storage media, or the like. The instructions may be executed to support one or more aspects of the functionality described in this disclosure.

The techniques described in this disclosure can be applied for electrical stimulation when the energy of requested electrical stimulation is greater than the maximum energy output of all the channels of IMD 14, or less than all of the channels of IMD 14 (e.g., a single channel), for electrical stimulation systems applicable to any of a wide variety of symptoms or conditions such as chronic pain, tremor, Parkinson's disease, epilepsy, urinary or fecal incontinence, sexual dysfunction, obesity, or gastroparesis. For example, the techniques may be applied to implantable medical devices configured to deliver neurostimulation or other electrical stimulation therapy via implanted electrode arrays, carried by leads or otherwise, located proximate to the spinal cord, pelvic nerves, peripheral nerves, the stomach or other gastrointestinal organs, or within the brain of a patient.

What is claimed is:

1. A method comprising:
    determining, by a processor, that an energy associated with a therapy program exceeds a threshold value, wherein therapy delivery to a patient by a medical device according to the therapy program generates a therapy field;
    responsive to the determination, generating, by the processor, at least a first subfield and a second subfield to decompose the therapy field; and
    outputting, by the processor and for display, the first subfield and the second subfield.

2. The method of claim 1, wherein the energy is a first energy and a second energy associated with the at least first subfield and second subfield is less than or equal to the first energy associated with the therapy program.

3. The method of claim 1, wherein the threshold value is based on a maximum energy output of a medical device that delivers therapy to a patient based on the therapy program or a channel of the medical device.

4. The method of claim 1, wherein the threshold value is based on an expected minimum energy value that a medical device can provide at the end of a predetermined time period, wherein the medical device delivers therapy to a patient based on the therapy program.

5. The method of claim 1, wherein the therapy program is a first therapy program, and wherein the method further comprises generating, by the processor, at least one second therapy program comprising one or more stimulation parameter value defining therapy delivery that generates the first subfield and the second subfield.

6. The method of claim 1, further comprising receiving, via a user interface comprising a representation of a lead, user input that defines at least a portion of the therapy field with respect to the lead, the therapy field being associated with the therapy program.

7. The method of claim 1, further comprising displaying the first subfield and the second subfield in conjunction with a representation of a lead.

8. The method of claim 1, further comprising receiving user input manipulating the first subfield to create a third subfield.

9. The method of claim 8, further comprising:
determining that an energy associated with the second subfield and the third subfield exceeds the threshold value; and
responsive to determining that the energy associated with the second subfield and the third subfield exceeds the threshold value, prompting a user to modify at least one of the second subfield or the third subfield.

10. The method of claim 8, further comprising:
determining that an energy associated with the second subfield and the third subfield exceeds the threshold value; and
responsive to determining that the energy associated with the second subfield and the third subfield exceeds the threshold value, generating, by the processor, at least a fourth subfield and a fifth subfield to decompose at least one of the second subfield or the third subfield.

11. A system comprising:
a memory configured to store a therapy program, wherein therapy delivery to a patient by a medical device according to the therapy program generates a therapy field; and
a processor configured to:
determine that a first energy associated with the therapy program exceeds to a threshold value,
responsive to the determination, generate at least a first subfield and a second subfield to decompose the therapy field, and
output, for display, the first subfield and the second subfield.

12. The system of claim 11, wherein the energy is a first energy and a second energy associated with the at least first subfield and second subfield is less than or equal to the first energy associated with the therapy program.

13. The system of claim 11, wherein the therapy program is a first therapy program, and wherein the processor is configured to generate at least one second therapy program comprising one or more stimulation parameter value defining therapy delivery that generates the first subfield and the second subfield.

14. The system of claim 11, further comprising a user interface configured to:
display a representation of a lead, and
receive user input defining at least a portion of the therapy field with respect to the lead, the therapy field being associated with the therapy program.

15. The system of claim 11, further comprising a display configured to present the first subfield and the second subfield in conjunction with a representation of a lead.

16. The system of claim 11, wherein the processor is configured to receive an indication of user input manipulating the first subfield to create a third subfield.

17. The system of claim 16, wherein the processor is configured to:
determine that an energy associated with the second subfield and the third subfield exceeds the threshold value, and
responsive to determining that the energy associated with the second subfield and the third subfield exceeds the threshold value, prompt, via a user interface, a user to modify at least one of the second subfield or the third subfield.

18. The system of claim 16, wherein the processor is configured to:
determine that an energy associated with the second subfield and the third subfield exceeds the threshold value, and
responsive to determining that the energy associated with the second subfield and the third subfield exceeds the threshold value, generate at least a fourth subfield and a fifth subfield to decompose at least one of the second subfield or the third subfield.

19. A non-transitory computer-readable medium comprising instructions that cause a programmable processor to:
determine that an energy associated with a therapy program exceeds a threshold value, wherein therapy delivery to a patient by a medical device according to the therapy program generates a therapy field;
responsive to the determination, generate at least a first subfield and a second subfield to decompose the therapy field; and
output, for display, the first subfield and the second subfield.

20. The non-transitory computer-readable medium of claim 19, wherein the threshold value is a maximum energy output of a medical device that delivers therapy to a patient based on the therapy program or a channel of the medical device.

* * * * *